US010679758B2

(12) United States Patent
Fox et al.

(10) Patent No.: US 10,679,758 B2
(45) Date of Patent: Jun. 9, 2020

(54) SYSTEM AND METHOD FOR SUPPORTING DECISIONS DURING A CATHETERIZATION PROCEDURE

(71) Applicant: Abbott Cardiovascular System Inc., Santa Clara, CA (US)

(72) Inventors: Julia C. Fox, San Carlos, CA (US); Peter Staehr, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1010 days.

(21) Appl. No.: 14/821,573

(22) Filed: Aug. 7, 2015

(65) Prior Publication Data
US 2017/0035514 A1    Feb. 9, 2017

(51) Int. Cl.
| | |
|---|---|
| *G06Q 10/10* | (2012.01) |
| *G06Q 10/06* | (2012.01) |
| *G06Q 30/02* | (2012.01) |
| *G06Q 30/06* | (2012.01) |
| *G06Q 10/08* | (2012.01) |
| *G16H 50/70* | (2018.01) |
| *G16H 10/60* | (2018.01) |
| *G16H 40/63* | (2018.01) |
| *G16H 30/40* | (2018.01) |
| *A61B 90/00* | (2016.01) |
| *A61M 25/01* | (2006.01) |
| *A61B 34/00* | (2016.01) |
| *A61B 90/96* | (2016.01) |
| *A61B 17/22* | (2006.01) |

(52) U.S. Cl.
CPC ............ *G16H 50/70* (2018.01); *G06Q 10/10* (2013.01); *G16H 10/60* (2018.01); *G16H 30/40* (2018.01); *G16H 40/63* (2018.01); *A61B 90/96* (2016.02); *A61B 2017/22051* (2013.01); *A61B 2034/256* (2016.02); *A61B 2090/376* (2016.02); *A61B 2090/3735* (2016.02); *A61B 2090/3782* (2016.02); *A61B 2576/00* (2013.01); *A61M 2025/0166* (2013.01)

(58) Field of Classification Search
CPC .......... G06Q 10/10; A61B 5/05; G06F 19/00; G16H 50/70; G16H 10/60; G16H 40/63; G16H 30/40; A61M 2025/0166
USPC .................... 705/1.1–912; 700/245; 600/424
See application file for complete search history.

(56) References Cited

U.S. PATENT DOCUMENTS

| | | | |
|---|---|---|---|
| 6,351,513 B1 * | 2/2002 | Bani-Hashemi | A61B 5/055 378/19 |
| 7,697,972 B2 * | 4/2010 | Verard | A61B 1/00071 600/407 |
| 9,314,311 B2 * | 4/2016 | Wenderow | A61B 5/7475 |
| 2002/0168618 A1 * | 11/2002 | Anderson | A61F 2/07 434/262 |

(Continued)

*Primary Examiner* — Jonathan P Ouellette
(74) *Attorney, Agent, or Firm* — Womble Bond Dickinson (US) LLP

(57) ABSTRACT

Methods and systems for facilitating clinical decisions during a catheterization procedure based at least in part on image data captured during the catheterization procedure, are disclosed. More particularly, embodiments include analyzing the image data and transmitting decision support data representative of past catheterization procedures having a similarity to the current catheterization procedure. Other embodiments are also described and claimed.

26 Claims, 17 Drawing Sheets

(56) References Cited

U.S. PATENT DOCUMENTS

2013/0024213 A1\* 1/2013 Poon ................... A61B 5/0002
705/3
2018/0182262 A1\* 6/2018 Keller ..................... G09B 7/04

\* cited by examiner

PATIENT DATA

- Age: 58 year old
- Gender: Male
- Medical History: Hyperlipidemia w/ Stable Angina
- Medications: Lovastatin 20 mg Daily

FIG. 5A

HISTORICAL INTERVENTION DATA 902

| Case Data | Patient Data | | | | Anatomical Data | |
|---|---|---|---|---|---|---|
| Unique Case Identifier (UCI) | Age | Gender | Medications | History | Diameter (mm) | Lesion Type |
| 20140813B15 | 58 | Male | N/a | N/a | 3.25 | B |
| 20140922P02 | 45 | Female | N/a | N/a | 3 | A |
| 20140222M45 | 62 | Male | Lovastatin | Hyperlipidemia | 3.5 | C |
| 20150316B08 | 58 | Male | Lovastatin | Hyperlipidemia | 3.25 | B |

CURRENT INTERVENTION DATA 904

| | Device Data | | Deployment Data | |
|---|---|---|---|---|
| Unique Device Identifier (UCI) | Device Type | Device Size (mm) | Apposition Percentage | Apposition Gap Distance (mm) |
| 56184735 | Stent, Bioabsorbable | 3.25 | 60% | 0.4 |
| 78914532 | PTCA | 3 | N/a | N/a |
| 75346589 | Stent, Metallic | 3.5 | 80% | 0.2 |
| 12463578 | Stent, Bioabsorbable | 3.25 | 50% | 0.5 |

FIG. 9

HISTORICAL INTERVENTION DATA
902

| | Procedural Data | | | |
|---|---|---|---|---|
| Interventional Step | Device Type | Device Size (mm) | Deployment Characteristic | Pre-Pos Anatomical Characteristic |
| Post-Dilatation | NC Balloon | 3.25 | 22 atm | 1.1 |
| N/a | N/a | N/a | N/a | 1.2 |
| Post-Dilatation | NC Balloon | 3.5 | 12 atm | 1.1 |
| - | - | - | - | - |

CURRENT INTERVENTION DATA
904

| Outcome Data | |
|---|---|
| Intra-Procedure Result | Inter-Procedure Result |
| Good Angiograph | 232 Day Readmission |
| Good Angiograph | 21 Day Readmission |
| Good Angiograph | 174 Day Readmission |
| - | - |

FIG. 9 (CONT.)

SYSTEM AND METHOD FOR SUPPORTING DECISIONS DURING A CATHETERIZATION PROCEDURE

BACKGROUND

Field

Embodiments related to facilitating clinical decisions during a medical procedure such as a current catheterization procedure are disclosed.

Background Information

Medical interventions, such as cardiac interventions, often include accessing anatomical sites within a patient to perform a surgical treatment. For example, catheterization procedures often include accessing anatomical sites within a human cardiovascular system to deploy a device, e.g., to deploy a stent to scaffold a lesion at the anatomical site. These interventions and procedures generally require performance of a sequence of operations in a treatment approach, and an outcome of the intervention depends on this approach. Determining the treatment approach, including the choice of accessory devices and procedural steps, is usually based on visual assessment or simple measurements taken during the intervention. Thus, achieving an optimal outcome is largely based on a subjective experience of the operator. For example, the operator may rely solely on his own personal education and experience to make decisions about what device to use or which operation to perform next during the catheterization procedure, based on his assessment of images showing the deployed device.

SUMMARY

Advances in computing technology have enabled the storage of large databases of structured and unstructured clinical information, including patient histories, lab results, and multi-modality image data. The information in these databases can be analyzed in an aggregated, de-identified way to provide decision support information to operators and improve patient outcomes. For example, these databases may be leveraged to identify historical intervention data with similarities to current intervention data, e.g., similar patient histories or similar image data, and the procedural characteristics and outcomes of the historical intervention data may be used to present treatment approaches to the operator and predict likely patient outcomes when the treatment approaches are followed in a current intervention. Thus, an operator may be provided with precise objective data, e.g., average 30-day readmission rates when the treatment approach is followed, which would be unavailable through the use of subjective experience alone. Accordingly, a decision support system may be provided to help operators make clinical decisions that adhere to best intervention practices and improve clinical outcomes.

In an embodiment, a method and system for facilitating clinical decisions during a catheterization procedure is provided. The method may include storing, in an interventional case history database, historical intervention data representative of past catheterization procedures. Current intervention data representative of a current catheterization procedure may be received concurrently with the current catheterization procedure, and stored in the interventional case history database along with the historical intervention data. The current intervention data may include image data representing an anatomical site being accessed during the current catheterization procedure. In an embodiment, the intervention data is analyzed. For example, the image data may be analyzed to determine additional intervention data representative of the current catheterization procedure. Furthermore, analysis of the historical and current intervention data may be performed to identify past catheterization procedures having a similarity to the current catheterization procedure. The similar past catheterization procedures may represent a subset of the entire group of past catheterization procedures, and historical intervention data representative of the subset may be transmitted as decision support data that identifies options for next procedural steps and indicates likely clinical outcomes associated with the steps.

In an embodiment, a type of data stored for historical intervention data may be the same as the type of data stored for current intervention data. For example, historical intervention data may include one or more of historical patient data, including patient history and lab results, historical anatomical data, historical device data, and historical deployment data representative of the past catheterization procedures. The current intervention data may include current patient data and current device data representative of the current catheterization procedure. Furthermore, the additional intervention data may include current anatomical data and current deployment data representative of the current catheterization procedure. More particularly, intervention data may include any information that is descriptive or characteristic of past or current catheterization procedures. For example, the current anatomical data may include one or more of a dimension of the anatomical site, the degree, eccentricity, and length of calcification at the anatomical site, or the presence of multi-vessel disease. The current deployment data may include a degree of malapposition of a medical device deployed at the anatomical site.

Historical intervention data may include some data types, however, that are not present in the current intervention data. For example, historical intervention data may include historical procedural data or historical outcome data representative of a treatment approach in the past catheterization procedures that has yet to be taken in the current catheterization procedure. These different data types may be transmitted as decision support data. For example, decision support data may include historical procedural data identifying an accessory device that can be used and/or a procedural step that can be performed during the current catheterization procedure. The decision support data includes historical outcome data having one or more of a median intra-procedure result or an average inter-procedure result when the procedural step was performed during the subset of past catheterization procedures. For example, the average inter-procedure result may include an average 30-day readmission rate for the subset of past catheterization procedures. Thus, the decision support data may support decisions about what procedural step to perform next and what the likely clinical outcome associated with the step may be.

In an embodiment, decision support data is provided by aggregating a subset of the historical intervention data that is representative of past procedures similar to the current procedure. Determining the similarity between the current catheterization procedure and the subset of past catheterization procedures may be based on matching one or more data values of the historical intervention data, the current intervention data, and the additional intervention data. For example, one or more sets of historical data values of the historical intervention data that match corresponding current data values of the current intervention data and the additional intervention data may be identified. Each set of matching data values may be assigned a similarity score. Then, the similarity between the current catheterization procedure and the subset of past catheterization procedures may be determined based on the similarity scores, e.g., whether a sum of the scores is above a predetermined similarity score threshold.

In an embodiment, the method and system for facilitating clinical decisions during a catheterization procedure is cloud-based and provides rapid feedback to operators across disparate geographies. For example, the historical intervention data may be stored at a location remote from a catheterization lab where the current catheterization procedure is being performed. Furthermore, transmission of the decision support data from the remote location may occur within five minutes of receiving the current intervention data from the catheterization lab over the internet.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

FIGS. 5A-5C show various graphical user interfaces displaying current intervention data for transmission to a server device in accordance with an embodiment.

FIG. 9 shows an interventional case history database in accordance with an embodiment.

DETAILED DESCRIPTION

Various embodiments and aspects of the invention will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present invention.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment. The processes depicted in the figures that follow may be performed by processing logic that comprises hardware (e.g. circuitry, dedicated logic, etc.), software, or a combination of both. Although the processes are described below in terms of some sequential operations, it should be appreciated that some of the operations described can be performed in a different order. Moreover, some operations can be performed in parallel rather than sequentially.

In an aspect, a decision support system facilitates clinical decisions during a catheterization procedure. The decision support system may incorporate computational models and predictive analytics to identify a treatment approach for a given patient and anatomy to result in a predicted favorable clinical outcome. The treatment approach may include identification of a subsequent device and/or accessory device to be used in the catheterization procedure. The treatment approach may identify a procedural step, e.g., a post-dilation step at a particular inflation pressure, to be followed next to achieve the predicted outcome. Accordingly, variation between operator practices and clinical outcomes may be reduced since decisions will be based on objective data rather than subjective experience. More particularly, by providing support to the operator throughout the catheterization procedure and leveraging the collective experience of the community of interventionists, the decision support system can improve adherence to best intervention practices and the latest treatment guidelines, and reduce hospital readmission rates. Furthermore, by making the decision support process more automated in nature as compared to basing choices entirely on remembered experiences and information, the decision support system may also save time and streamline the interventional process.

Figure 1:
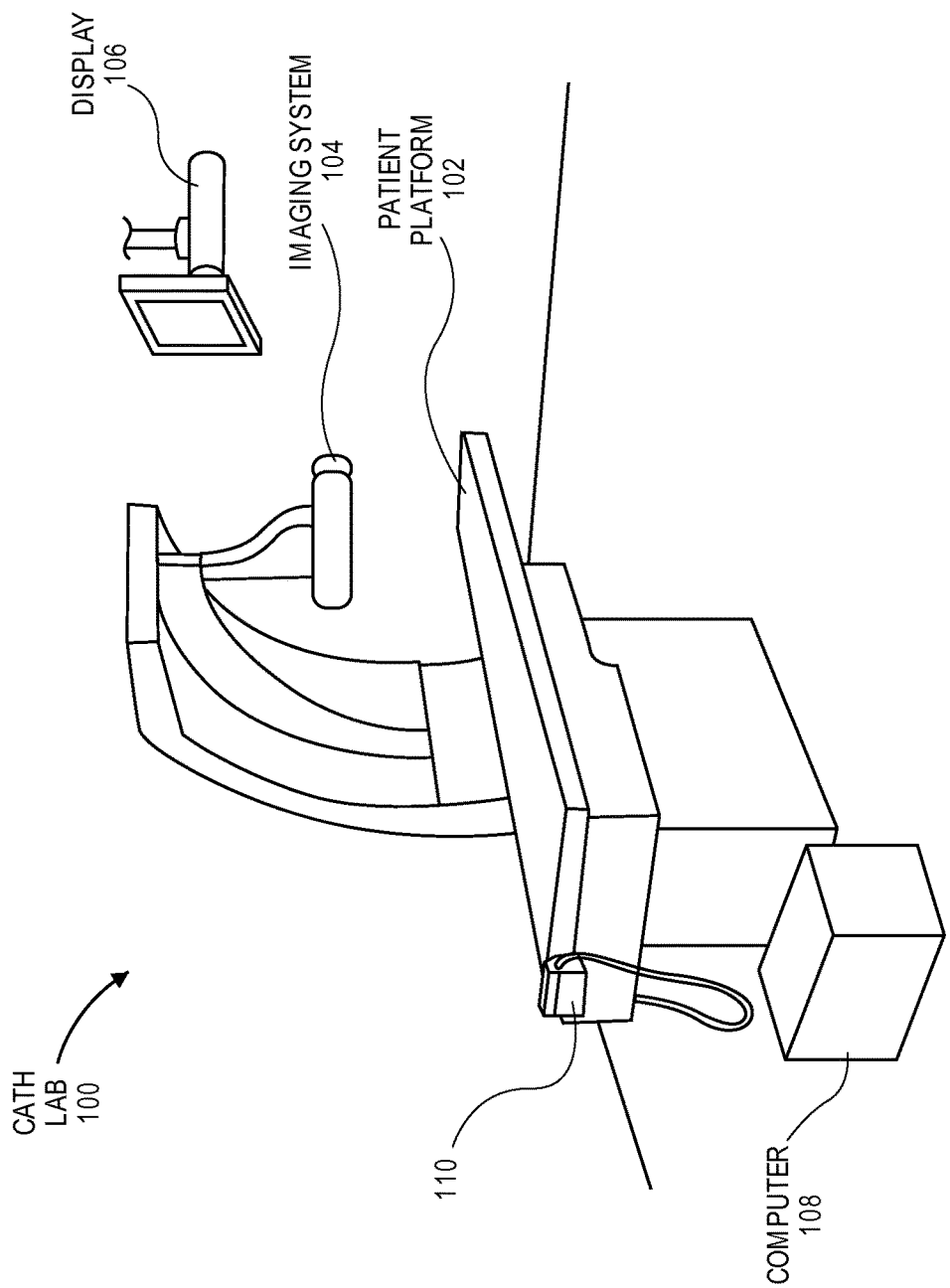
FIG. 1 is a pictorial view of catheterization lab where a catheterization procedure is performed in accordance with an embodiment.

Referring to FIG. 1, a pictorial view of a catheterization lab where a catheterization procedure is performed is shown in accordance with an embodiment. A catheterization lab 100 may include medical, diagnostic, and computer equipment to facilitate a medical intervention, such as a catheterization procedure. For example, medical equipment may include a table 102 for a patient to lay on during the catheterization procedure. Diagnostic equipment may include imaging equipment for performing various imaging modalities during the catheterization procedure. The imaging equipment may include injector pumps for delivering imaging contrasts to the patient, as well as an imaging system 104, such as a fluoroscope, an intravascular ultrasound (IVUS) system, an Optical Coherence Tomography (OCT) system, a Computed Tomography Fractional Flow Reserve (CT-FFR) system, echocardiography, or another type of imaging system 104 to enable other imaging modalities, e.g., angioscopy or RF backscatter virtual histology. One or more display devices 106 may be used to output images captured by imaging system 104, or other information, to an operator during the catheterization procedure. The images may be visual representations of processed image data that is captured from the imaging system 104. The image data may be stored as an image file in one or more computers 108. More particularly, the image data may be intervention data representative of the catheterization procedure, and may be stored with other such data. For example, one or more input devices 110, such as a barcode reader, may be used to receive data inputs, e.g., Unique Device Identifiers (UDI) or barcode information from medical devices used during the catheterization procedure, and the data inputs may be stored in computer 108 as intervention data representative of the catheterization procedure.

Figure 2:
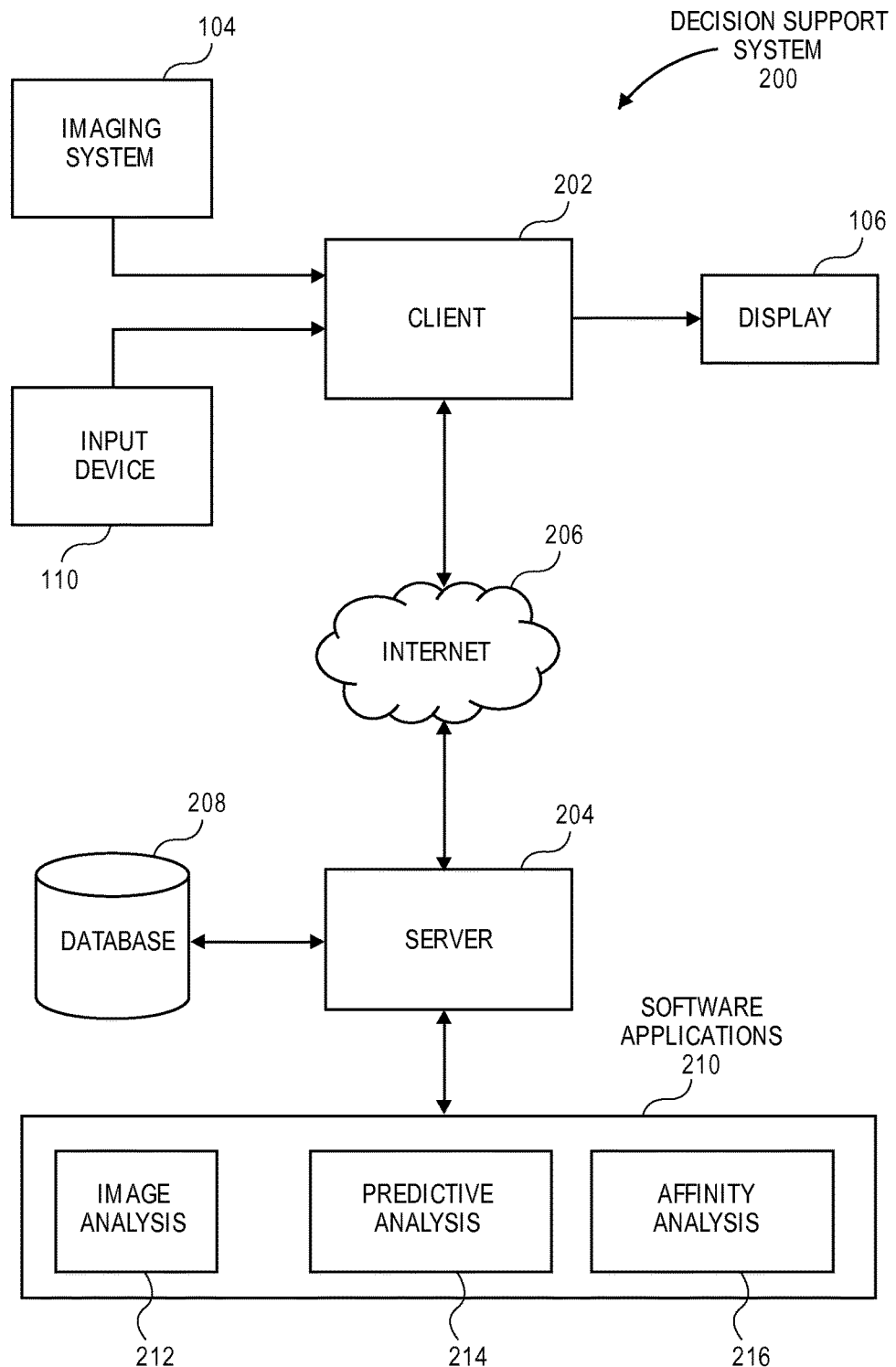
FIG. 2 is a schematic view of a decision support system to facilitate clinical decisions during a catheterization procedure in accordance with an embodiment.

Referring to FIG. 2, a schematic view of a decision support system to facilitate clinical decisions during a catheterization procedure is shown in accordance with an embodiment. A decision support system 200 may include a client-side and a server-side. For example, the client-side may include a client 202, which may include a device such as a desktop computer, laptop computer, tablet device, or smartphone device. The server-side may include a server 204, which may include one or more computers hosting software applications 210 to serve the requests of client 202. Client 202 and server 204 may be configured to connect with each other over a network, such as the internet 206. Accordingly, client 202 and server 204 may be internet-enabled and capable of communicating over the internet such that the decision support system 200 is cloud-based.

Client 202 may be situated in catheterization lab 100, which may be in a first geographic location, e.g., on the premises of a hospital. Client 202 may be configured to receive data inputs representative of a catheterization procedure. For example, client 202 may communicate with imaging system 104 to receive image data representing an anatomical site being accessed during the catheterization procedure. Furthermore, client 202 may communicate with input devices 110, e.g., barcode scanners, keyboard devices, touchscreen display devices, etc., to receive active input from an operator, e.g., a typed keyboard entry, or passive input from objects within catheterization lab 100, e.g., scanned input data from a barcode on a device package. The image data and the input data may be portions of intervention data. Intervention data may be representative of the catheterization procedure because it may represent characteristics of the catheterization procedure, including information about the patient, information about the devices used during the catheterization procedure, information about the anatomical site being accessed during the catheterization procedure, information about deployment of the devices during the catheterization procedure, etc. Client 202 may store and/or transmit the intervention data. For example, the intervention data may be transmitted over the internet 206 to server 204.

Server 204 may be located at a second geographic location remote from the first geographic location of client 202. For example, server 204 may include one or more computers located outside of the catheterization lab 100 or off the premises of the hospital. Server 204 may be configured to receive the intervention data from client 202. Furthermore, server 204 may be networked with other client devices located in other catheterization labs at geographically diverse locations such that server 204 receives intervention data representative of an array of different catheterization procedures, both past and present. The intervention data from client 202 in catheterization lab 100 and the intervention data from the array of other catheterization procedures may be stored in an intervention case history database 208 at the server 204. Furthermore, server 204 may be running instances of software applications 210 for performing computing processes on the intervention data stored in the intervention case history database 208. For example, server 204 may be running an instance of an image analysis software application or software module 212 for performing image registration, thresholding, pattern recognition, digital geometry, or other processing of image data stored in intervention case history database 208. The image analysis may generate additional intervention data, e.g., anatomical data or device delivery data representative of the catheterization procedure. Server 204 may also be running an instance of a predictive analysis software application or software module 214 for analyzing the intervention data stored in the intervention case history database 208. The predictive analysis may generate predictions about the future, e.g., the probable patient outcomes based on a recommended treatment approach. Additionally, server 204 may be running an instance of an affinity analysis software application or software module 216 for analyzing the intervention data stored in the intervention case history database 208. The affinity analysis may generate similarity relationships between different catheterization procedures that may be leveraged to make recommendations regarding, for example, next procedural steps, devices, or accessory devices to be used in a catheterization operation to increase a likelihood of favorable patient outcomes. Other software applications 210 may be run by server 204 in accordance with the description below.

Figure 3:
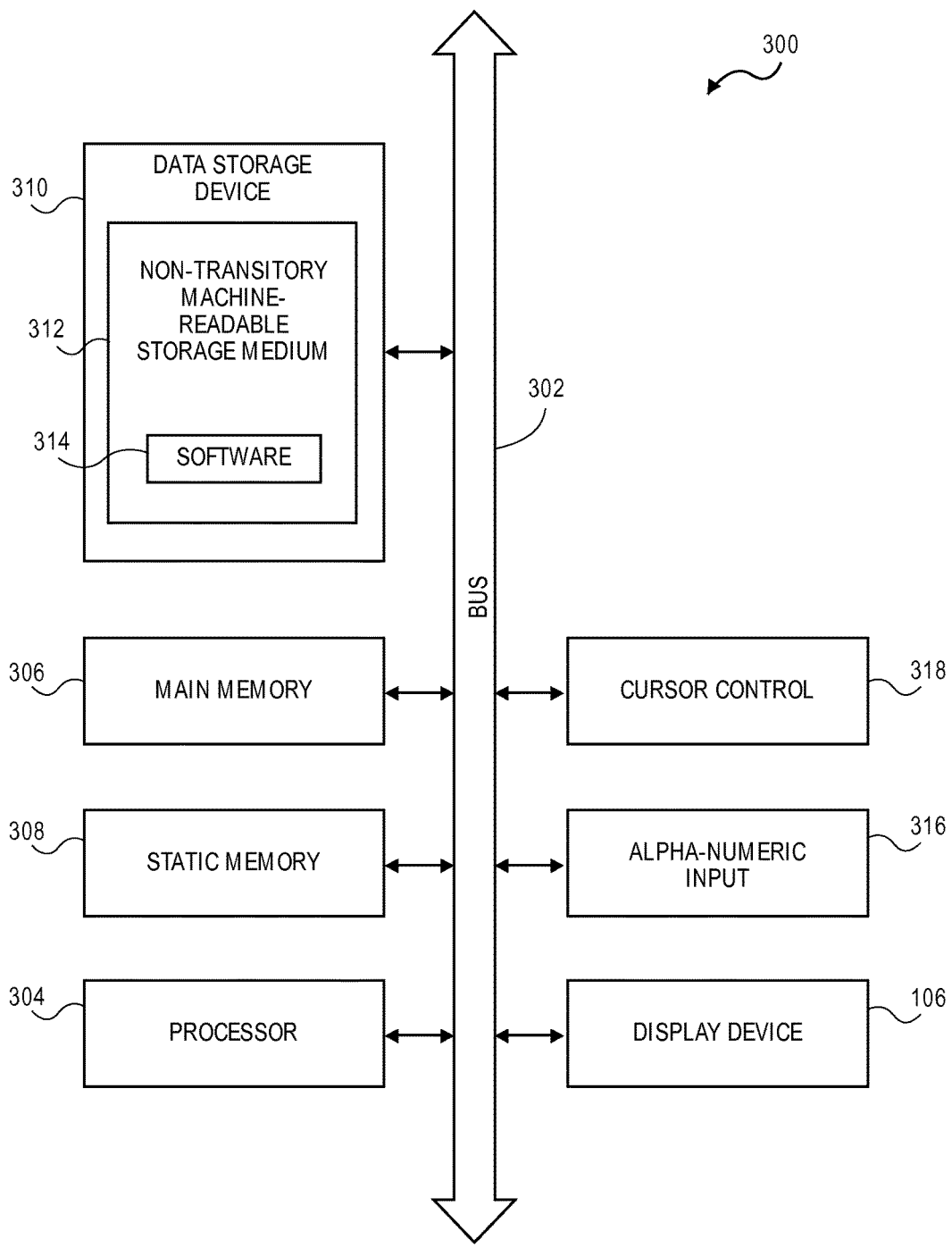
FIG. 3 is a schematic view of a computer system in accordance with an embodiment.

Referring to FIG. 3, a schematic view of a computer system is shown in accordance with an embodiment. Client 202 or server 204 may include one or more devices and/or computers having a processing system 300 that includes the illustrated system architecture. For example, computer 108 may include processing system 300. Furthermore, such a processing system 300 can implement the software applications and the methods referred to herein, such as software applications 210. Certain standard and well-known components which are not germane to the present invention are not shown.

Processing system 300 includes an address/data bus 302 for communicating information, and one or more processors 304 coupled to bus 302 for processing information and instructions. Processing system 300 may also include data storage features such as main memory 306 having computer usable volatile memory, e.g. random access memory (RAM), coupled to bus 302 for storing information and instructions for processor(s) 304, static memory 308 having computer usable non-volatile memory, e.g. read only memory (ROM), coupled to bus 302 for storing static information and instructions for the processor(s) 304, and a data storage device 310 (e.g., a magnetic or optical disk and disk drive) coupled to bus 302 for storing information and instructions.

Data storage device 310 may include a non-transitory machine-readable storage medium 312 storing one or more sets of instructions (e.g. software 314) embodying any one or more of the methodologies or operations described herein. Software 314 may include software applications 210 described above, for example. Software 314 may also reside, completely or at least partially, within main memory 306, static memory 308, and/or within processor(s) 304 during execution thereof by processing system 300. More particularly, main memory 306, static memory 308, and processor(s) 304 may also constitute non-transitory machine-readable storage media.

Processing system 300 of the present embodiment also includes input devices 110 for receiving active or passive input. For example, an alphanumeric input device 316 may include alphanumeric and function keys coupled to bus 302 for communicating information and command selections to processor(s) 304. Alphanumeric input device 316 may include input devices of various types, including keyboard devices, touchscreen devices, or voice activation input devices, to name a few types. Processing system 300 may also include a cursor control device 318, e.g., a mouse device, coupled to bus 302 for communicating user input information and command selections to processor(s) 304. Processing system 300 may include a display device 320, such as display 106 described above, which may be coupled to bus 302 for displaying information to an operator.

Figure 4:
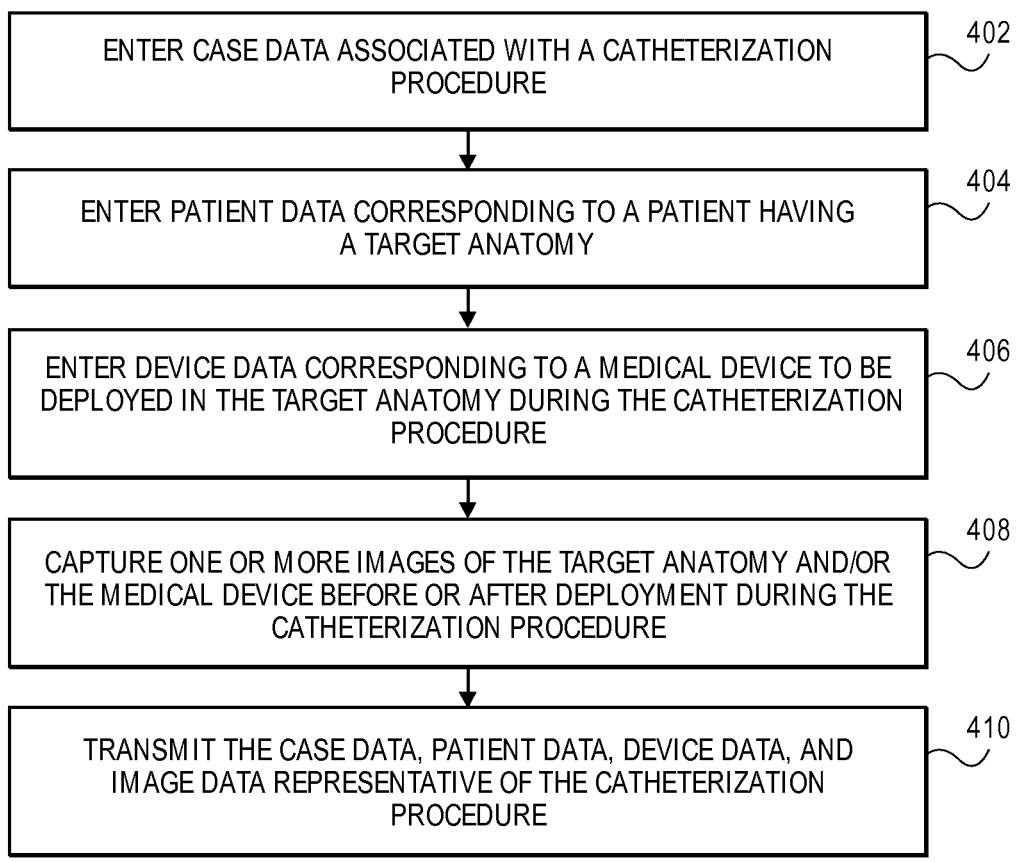
FIG. 4 is a flowchart of a method to transmit current intervention data from a client device to a server device in accordance with an embodiment.

Referring to FIG. 4, a flowchart of a method to transmit current intervention data from a client device to a server device is shown in accordance with an embodiment. In an embodiment, a catheterization procedure may be performed in catheterization lab 100 to treat a cardiovascular condition of a patient. For example, the catheterization procedure may be a percutaneous coronary intervention (PCI) to treat a stenosis, i.e., a lesion, in a blood vessel of the patient. Alternatively, the catheterization procedure may be a heart valve clip implantation procedure to treat mitral valve regurgitation in the patient. Thus, the catheterization procedure may be performed to percutaneously access an anatomical site in the patient, and possibly, to perform one or more procedures after accessing the site, e.g., crossing a lesion, implanting a stent, expanding a balloon, deploying a clip, etc., to treat the cardiovascular condition.

Prior to, or during, the catheterization procedure, an operator or catheterization lab staff may input intervention data associated with the catheterization procedure into client 202. For example, the operator may enter one or more of case data, patient data, device data, or anatomical data associated with the catheterization procedure. In an embodiment, the intervention data, including the case data, patient data, or device data, is input manually by an operator using an input device 110, such as an alpha-numeric input device 316. That is, the operator may manually type the information using a keyboard device to input the data into client 202. In another embodiment, the intervention data is automatically input using an input device 110, such as a barcode scanner. That is, the operator may use a barcode scanner to read and decode barcode data for entry into client 202. The input data may be received and stored by client 202.

At operation 402, the operator enters case data representative of the catheterization procedure. In an embodiment, case data includes information about the catheterization procedure. For example, case data may include a unique case identifier (UCI). A UCI may be an identifier that uniquely identifies the catheterization procedure from all other past catheterization procedures. For example, the UCI may include a string of data corresponding to a combination of a date on which the catheterization procedure is being performed and a unique patient identifier, e.g., some portion of the patient's social security number, the combination of which neither has or will occur again. Since the UCI uniquely identifies a catheterization procedure, it may be used as a key in intervention case history database 208 when analyzing data records.

In addition to a UCI, case data may include other case-related metadata, such as individual entries for the date on which the catheterization procedure is being performed, a hospital, city, and/or state where the procedure is being performed, the operator performing the procedure, etc. Case data may be entered manually through an alpha-numeric input device 316 such as a keyboard device or a touchscreen panel. Alternatively, case data may be entered automatically, e.g., by scanning a barcode on a wristband worn by the patient to receive UCI data encoded in the barcode pattern.

At operation 404, the operator enters patient data representative of the patient being treated during the catheterization procedure, i.e., having the target anatomy. In an embodiment, patient data includes information about the patient undergoing the catheterization procedure. Patient data may include a variety of patient-specific characteristics, such as an age or sex of the patient. Patient data may also include patient-specific historical data, such as medications that the patient is currently taking, known medical conditions that the patient has and/or had, and any diagnostic data. Patient data may be generic, i.e., de-identified such that the data stored in intervention case history database 208 does not identify a particular actual person. The patient data may nonetheless include a unique patient identifier (UPI) that uniquely identifies the patient. For example, in an embodiment, the UPI identifies a patient using the patient's social security number.

Referring to FIG. 5A, a graphical user interface displaying current intervention data for transmission to a server device is shown in accordance with an embodiment. As discussed above, patient data may be entered by an operator using input device 110 and the entered data may be displayed for visual confirmation and/or editing by the operator before transmitting the entered data from client 202 to server 204. Patient data may include age, sex, medical history data (including information about symptoms and/or underlying conditions and diagnostic data), or medication data (including information about types of medications prescribed, amount per time period prescribed, and other prescription information), as shown.

Referring again to FIG. 4, at operation 406, the operator enters device data corresponding to one or more devices being used during the catheterization procedure. In an embodiment, device data includes information about one or more of the devices being deployed in the target anatomy during the catheterization procedure. For example, device data may include a unique device identifier (UDI). A UDI may be an identifier that uniquely identifies a device being used in the catheterization procedure from all other devices used in past catheterization procedures. For example, the UDI may include a string of data corresponding to a combination of a manufacturer, a part number, and a serial number of the device, the combination of which neither has or will be used in the manufacture of another device. Since the UDI uniquely identifies a device used in a catheterization procedure, it may be used as a key in intervention case history database 208 when analyzing data records.

In addition to a UDI, device data may include other device-related metadata, such as individual entries for the manufacturer, the part number, or the serial number of the device. Device data may describe the type of device, e.g., a bioabsorbable stent/scaffold, a percutaneous transluminal coronary angioplasty (PTCA) balloon, a metallic stent, a guidewire, a microcatheter, a percutaneous mitral valve repair system, etc. Device data may include dimensional characteristics of the device, e.g., a nominal device size such as a nominal deployment length or diameter of the device as specified by the manufacturer.

Figure 5B:
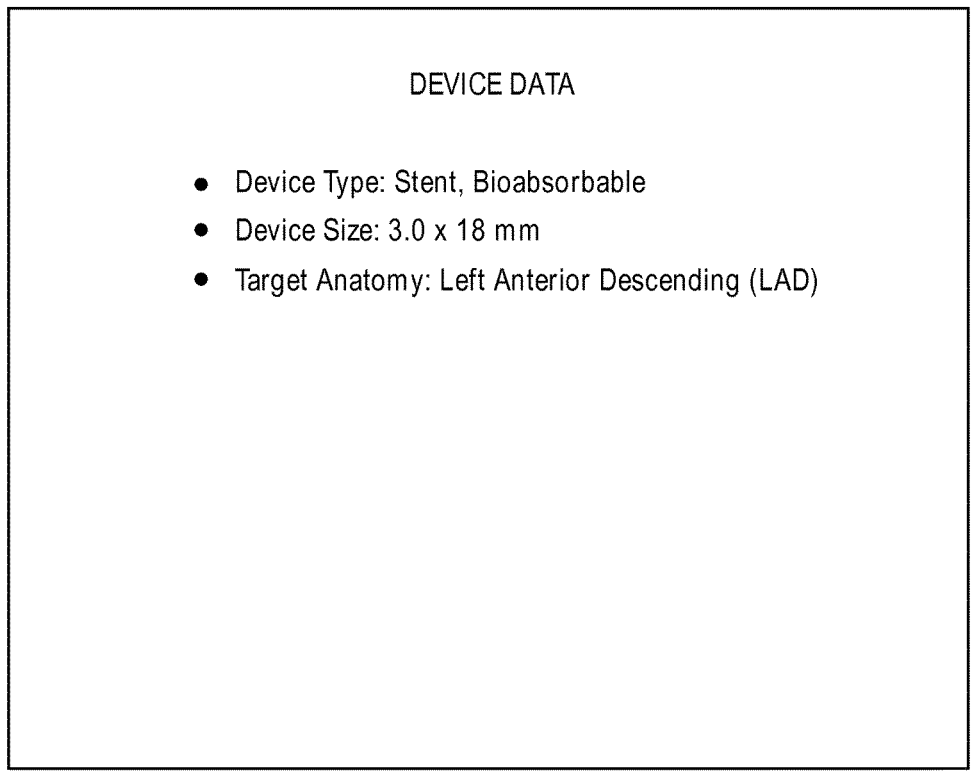

Referring to FIG. 5B, a graphical user interface to displaying current intervention data for transmission to a server device is shown in accordance with an embodiment. As discussed above, device data may be entered by an operator using input device 110 and the entered data may be displayed for visual confirmation by the operator before transmitting the entered data from client 202 to server 204. Device data may include a type of device (including device genus information, e.g., "stent", and device species information, e.g., "bioabsorbable"), device size (including specified deployment size and length), and a target anatomy for the device, such as a specific coronary vessel or other well-defined anatomical location, as shown.

Figure 5C:
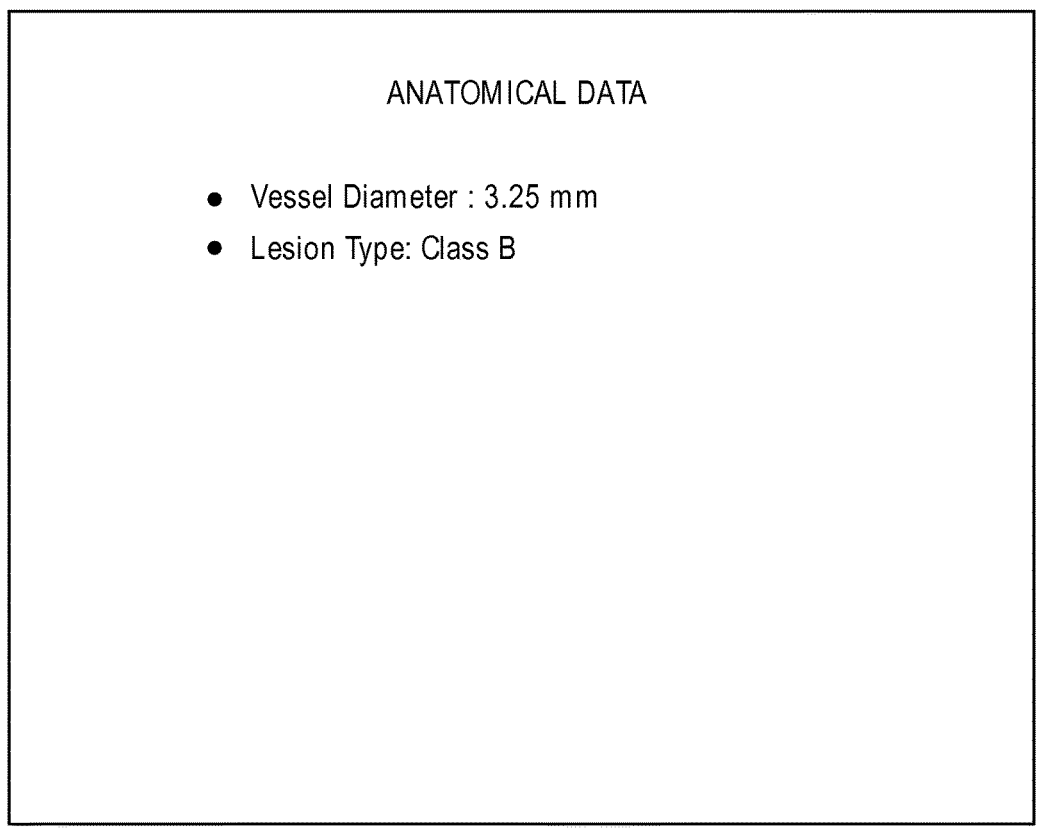

Referring to FIG. 5C, a graphical user interface to displaying current intervention data for transmission to a server device is shown in accordance with an embodiment. Intervention data may include data types other than those discussed above. For example, in addition to patient data or device data, an operator may enter data corresponding to a target anatomy for the interventional procedure. The target anatomy may be measured or assessed using imaging system 104 to determine quantitative data, such as vessel diameter, or qualitative data, such as a lesion type or class. The measured/assessed data may be input by the operator using input device 110, and visually confirmed and/or edited using display device 106, which displays the entered data prior to transmitting the current intervention data to server 204.

Anatomical data entered by the operator may include morphological information. For example, information about the target anatomy morphology, e.g., the vasculature, may be input. Such morphological information may include lesion length, the presence and dimensions of any side branches, the type of side branch or bifurcation (e.g., Medina classification), presence of multi-vessel disease etc. More particularly, any morphological information with predictive value in terms of being a contributing factor to interventional complexity or outcomes may be input as part of the anatomical data entered by the operator. Such morphological information may also be automatically recognized using image analysis tools, as described below with respect to producing additional intervention data by the server.

Certain angiographic baseline variables are commonly collected for evaluation by a core lab during a clinical trial, and thus, are specifically contemplated as being within the ambit of anatomical data that may be collected (either by manual entry or automatic image analysis) during a current catheterization procedure. These variables are listed here by way of example, and not limitation: vessel or lesion location (e.g., coronary artery surgery study (CASS) location, or ostial, proximal, medial, or distal), lesion length, reference vessel diameter (RVD), percent diameter stenosis (prior to any treatments), TIMI flow, lesion concentricity/eccentricity, vessel bend (angulation), thrombus presence/type, tortuosity characteristics, calcification (none, mild, moderate, or severe), aneurysm presence, or presence of a dissection. These and other lesion characteristics will be understood by one skilled in the art and may be captured for evaluation according to this description.

In addition to the lesion characteristics noted above, as well as the patient data described previously, clinical characteristics may also be collected manually or automatically for the case evaluation in comparison to historical data. Among the relevant clinical characteristics that may be included in current and historical intervention data are by way of example, and not limitation: baseline symptoms of the patient, patient history, patient diagnostic data, patient age, extent and severity of ischemia (e.g., measured by CT-FFR, electrocardiogram (ECG) stress test, stress echo, etc.). Additional information that may be useful includes whether the patient has experienced a prior myocardial infarction (MI), ventricular ejection fraction, renal function (e.g., creatinine, clearance, etc.). These and other clinical characteristics will be understood by one skilled in the art and may be captured for evaluation according to this description.

Figure 6:
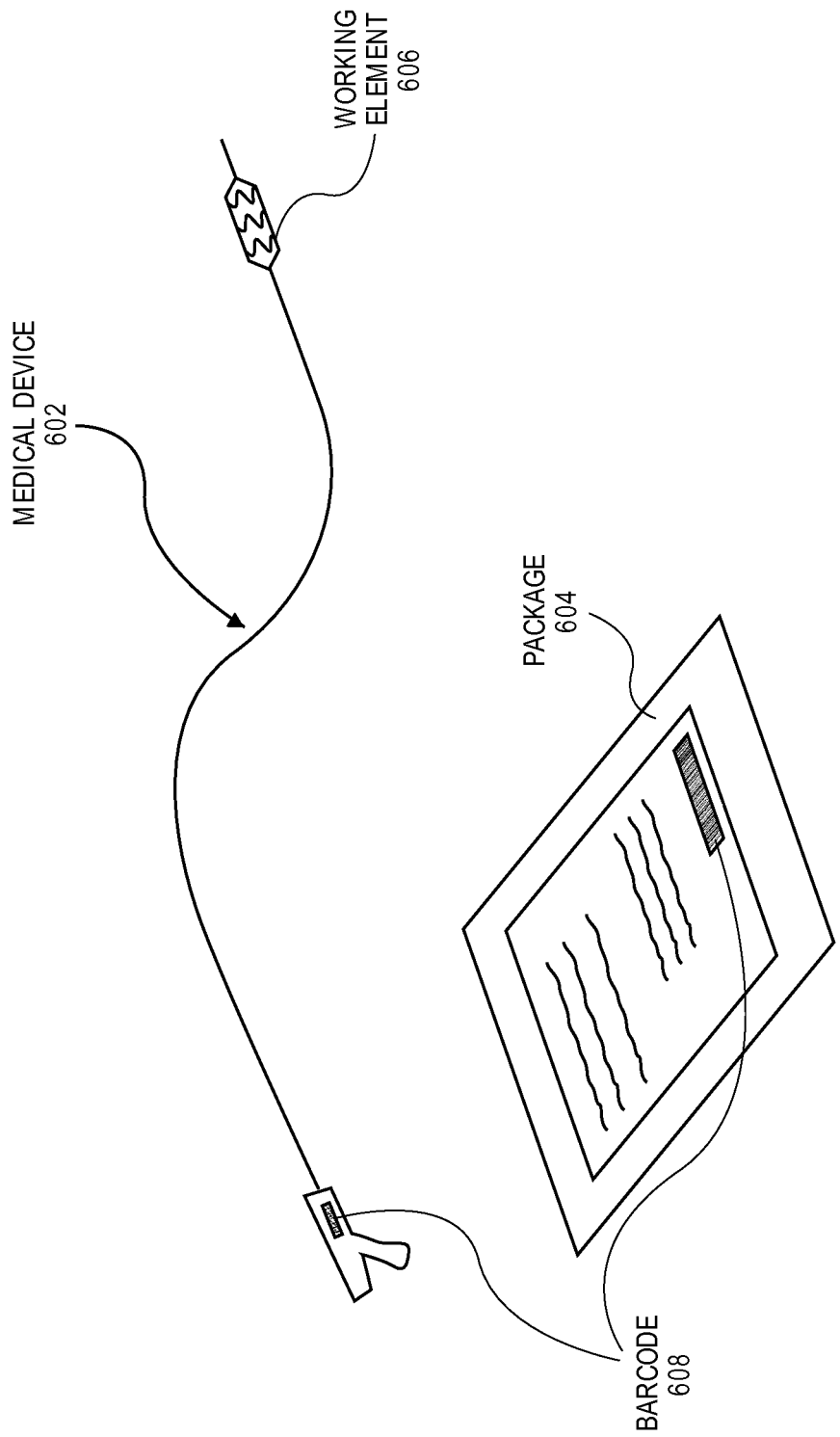
FIG. 6 is a pictorial view of a medical device and a medical device package used during a catheterization procedure in accordance with an embodiment.

Referring to FIG. 6, a pictorial view of a medical device and a medical device package used during a catheterization procedure is shown in accordance with an embodiment. The intervention data represented in FIGS. 5A-5C may be manually entered as discussed above prior to or during the catheterization procedure. In an embodiment, manually entered data is combined with automatically entered data. For example, a medical device 602 being used during the catheterization procedure may be removed from a package 604 in catheterization lab 100. Medical device 602 may include a working element 606, e.g., an implant, a balloon, a valve clip, etc., for delivery at a target anatomical site. In an embodiment, medical device 602 is a guidewire without working element 606. One or more of medical device 602 or package 604 may further include a barcode 608 containing encoded data, such as device data, and the encoded data may be read and decoded by input device 110, such as a barcode scanner, as discussed above. Thus, intervention data, such as device data displayed in FIG. 5B, may include a combination of manually and automatically input data describing one or more characteristics of the catheterization procedure.

Figure 7:
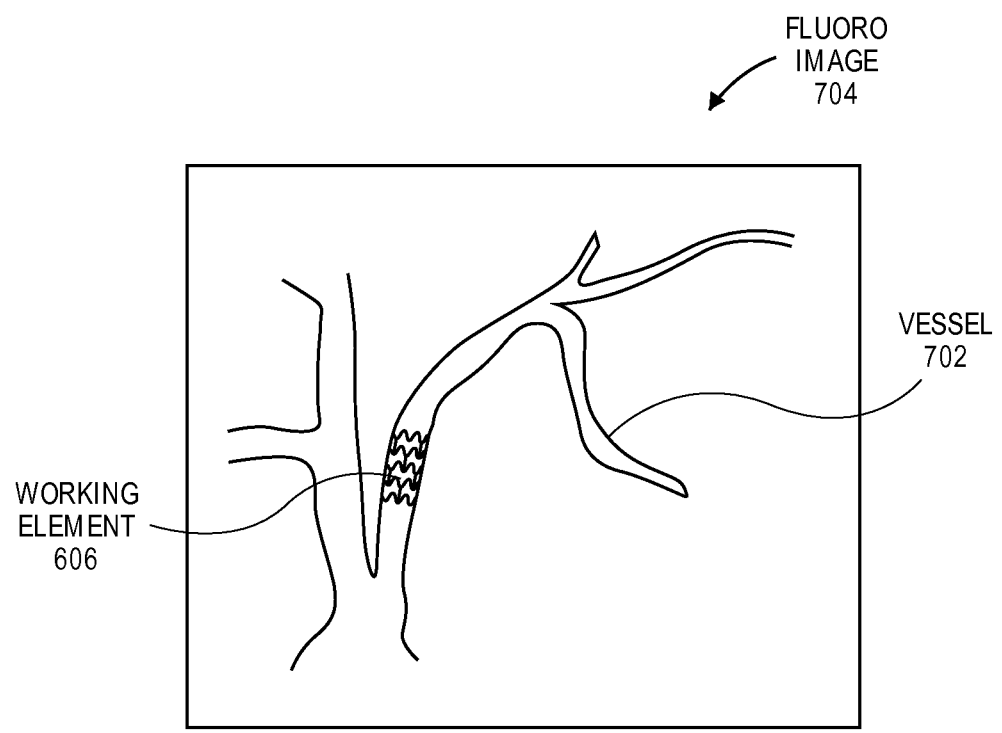
FIG. 7 shows an image captured during a catheterization procedure in accordance with an embodiment.

Referring again to FIG. 4, at operation 408, one or more images are captured during the catheterization procedure. Images may be captured using one or more imaging systems 104 to gather image data representing an anatomical site being accessed during the catheterization procedure. Image data may be representative of a target anatomical site prior to deployment of medical device 602, such as a chronic total occlusion (CTO) that the operator needs to cross during the catheterization procedure. Image data of the target anatomical site may also be captured after deployment of medical device 602, such as a coronary vessel or valve within which an implant is to be, or has been, deployed. Thus, one or more images may be captured of the target anatomy during the catheterization procedure. Alternatively, image data may be representative of a device, such as medical device 602 and/or working element 606 before or after being deployed at the target anatomical site. That is, one or more images may be captured of medical device 602 when it is to be deployed and/or deployed in the target anatomy during the catheterization procedure. Thus, image data may include information about the anatomical site or medical devices 602 used during the catheterization procedure Referring to FIG. 7, an image captured during a catheterization procedure is shown in accordance with an embodiment. Imaging equipment may include a fluoroscope capable of generating an extravascular view of medical device 602 deployed in a vessel 702. The extravascular view may be represented in a fluoroscopic image 704 displayed on display device 320. Imaging equipment may provide other imaging modalities, such as CT-FFR imaging, optical coherence tomography (OCT) imaging, IVUS imaging, and echocardiography, and thus the image data may be represented in other kinds of images (non-fluoroscopic images) displayed on display device 320. For example, in an embodiment, imaging equipment includes an IVUS system capable of generating an intravascular view of medical device 602 and/or working element 606 deployed in vessel 702. The intravascular view may be represented in an IVUS image displayed on display device 320 to view, e.g., apposition of a deployed implant relative to an inner wall of vessel 702, calcification of a vessel 702, etc. The captured images may be input and stored at client 202 as a portion of the intervention data representing the catheterization procedure.

A brief overview of certain imaging modalities shall now be provided, and one skilled in the art will understand that the following descriptions are representative and not exhaustive. IVUS may use a catheter guide ultrasound probe to emit sound waves, which bounce back echoes that are received and processed for display on a monitor. Different tissues have different echoes, e.g., IVUS can allow an operator to distinguish vascular plaque from normal endothelial lining. More particularly, IVUS may have a higher resolution than angiography and allow identification of plaques that are not seen angiographically. By way of example, normal healthy tissue/blood may be echolucent, and appear as black space in a displayed image, and calcification may be echogenic and appear as a bright area with black shadows behind in the displayed image. IVUS can allow for lesion assessment, vessel sizing, cross-section area determination, atheroma visualization, determining plaque morphology, assessing stent apposition or underexpansion, predicting stent thrombosis, and identifying dissection.

OCT may include a catheter-based imaging system that uses light in the near infrared spectrum to penetrate tissue up to 3 mm and to receive and process backscattered light from the vessel wall for displaying an image on a monitor. OCT can provide accurate assessment of the target lumen geometry, and the extent and severity of disease. OCT may also provide detailed stent strut evaluation, including defining measurement of stent area and diameters. In fact, OCT may detect stent strut apposition better than IVUS. OCT may also detect dissection and may be able to evaluate tissue coverage during follow up procedures, and evaluate bioresorbable scaffolds.

FFR may be measured to determine the fraction of maximal achievable blood flow that can still be maintained to the myocardium despite the presence of a stenosis. More particularly, FFR equals a pressure distal to a lesion measured by a pressure wire divided by a pressure at a tip of a guide/catheter. This measurement may be used as a surrogate marker of relative ischemia during exercise. In an embodiment, FFR is measured with a guidewire, e.g., a 0.014-inch coronary guidewire, with a miniaturized, high fidelity pressure sensor mounted proximal from a tip of the guidewire. The pressure drop across a lesion is proportional to a lesion length and flow across the lesion, and it is inversely related to the square root of the area of the stenosis. Thus, by measuring pressures on either side of a lesion, FFR may be determined and used to make a clinical judgment regarding whether to revascularize.

Referring again to FIG. 4, at operation 410, the intervention data representative of the catheterization procedure is transmitted from client 202 to server 204. The transmitted data may include one or more of the case data, patient data, device data, and image data that was input to client 202 manually and/or automatically, using input device 110 and/or imaging equipment. Data may be transmitted over the internet 206 from client 202, which is located at a first geographic location such as at a hospital, to server 204, which is located at a second geographic location remote from the first geographic location such as at a data server 204 maintained by an enterprise separate from the hospital. For example, the enterprise may be a medical device manufacturer or a company that provides cloud computing services such as Infrastructure as a Service (IaaS) or Platform as a Service (PaaS) cloud computing.

Figure 8:
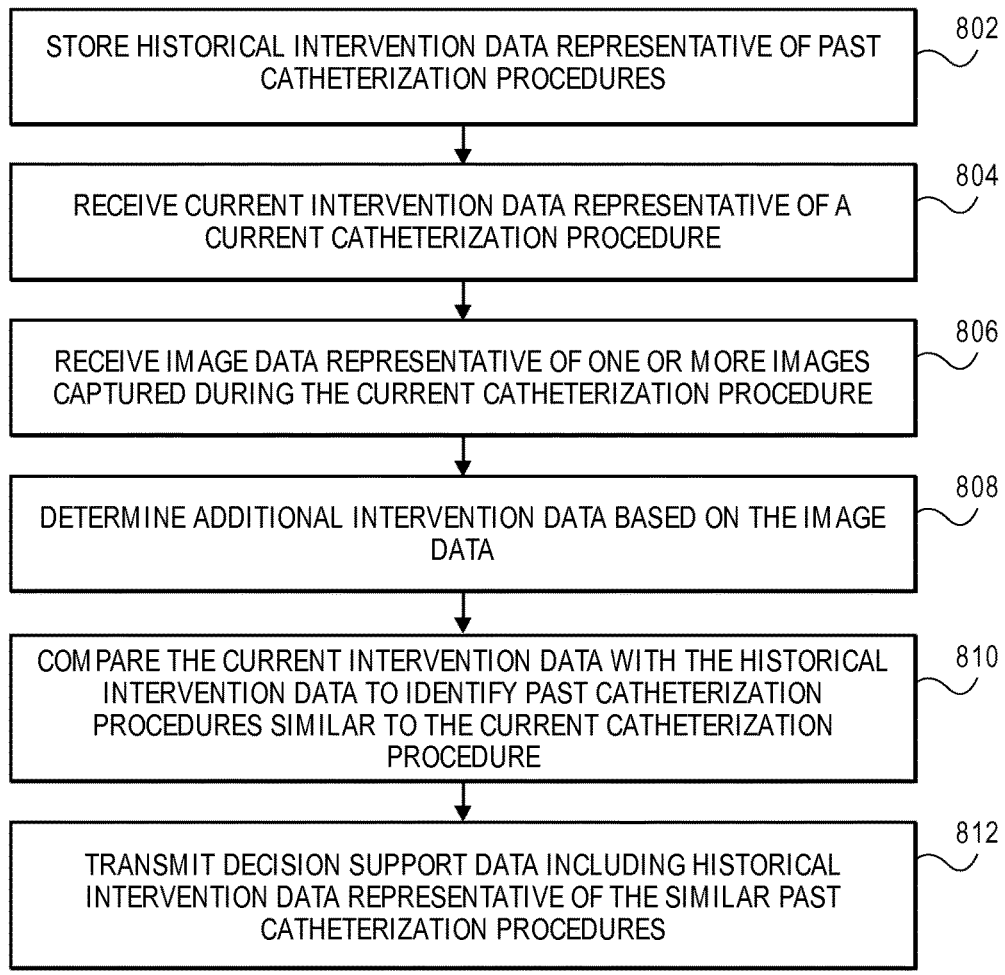
FIG. 8 is a flowchart of a method to determine and transmit decision support data to facilitate clinical decisions during a catheterization procedure in accordance with an embodiment.

Referring to FIG. 8, a flowchart of a method to determine and transmit decision support data to facilitate clinical decisions during a catheterization procedure is shown in accordance with an embodiment. At operation 802, server 204 stores data that is representative of catheterization procedures. For example, historical data may be stored that includes information about past catheterization procedures. The stored historical data may include the same type of data gathered for the catheterization procedure discussed above.

Referring to FIG. 9, an intervention case history database is shown in accordance with an embodiment. Server 204 may store historical intervention data 902 representative of the past catheterization procedures in intervention case history database 208. Historical intervention data 902 records representative of the past catheterization procedures may include historical case data, historical patient data, historical anatomical data, and historical device data input during the past catheterization procedures. Furthermore, historical data may be derived from the input data. For example, as described below, image data collected during catheterization procedures may be analyzed by software applications 210 to determine additional data such as historical deployment data or historical anatomical data. Derived historical deployment data may include information such as a degree of malapposition of a medical device 602 deployed at a target anatomical site or a gap distance between the medical device 602 and the anatomical site. Derived historical anatomical data may include information such as dimensions of the target anatomical site, the degree, eccentricity, and length of calcification at the anatomical site, or the presence of multi-vessel disease.

Historical intervention data 902 records may include data entries in intervention case history database 208 that are not associated with a current intervention data 904 record. For example, historical intervention data 902 records may include procedural data associated with respective UCIs and representative of procedural actions taken in the past catheterization procedures that have not yet been taken in the current catheterization procedure. As an example, in past catheterization procedures involving deployment of a stent implant at a target anatomy, a next step after deploying the implant may involve post-dilatation of the stent. As another example, in past catheterization procedures involving treatment of mitral valve regurgitation by deployment of a clip at the mitral valve, a next step after deploying the clip may involve repositioning the clip or deploying another clip. Thus, procedural data collected during the past catheterization procedures may include information describing the procedural action, including intervention steps (e.g., post-dilatation or "n/a" when no further steps were required), a device type used during the intervention steps (e.g., a non-compliant balloon catheter, a second stent system, etc.), a device size (e.g., a specified deployment diameter of the subsequent device), a deployment characteristic (e.g., an inflation pressure used by an operator to deploy the subsequent device), etc. This procedural data is discussed by way of example, and any other information related to procedural actions taken during the past catheterization procedures may be included in intervention case history database 208. Furthermore, the procedural data may include data derived from data gathered during the past catheterization procedures. For example, images captured during subsequent procedural steps may be analyzed to determine procedural characteristics such as pre-post anatomical characteristics, e.g., a ratio of a vessel diameter after post-dilatation compared to the vessel diameter before post-dilatation. Thus, procedural data may essentially provide a journal of information related to critical procedural steps taken during each catheterization procedure and how they were performed so the most successful of these procedures may be leveraged as strategic models for next steps in the current catheterization procedure.

Procedural data including procedural steps taken in the current catheterization procedure may be continually updated as additional actions are taken by an operator in catheterization lab 100. Thus, current intervention data 904 record may continue to populate with additional data as the catheterization procedure progresses. In the view shown, however, it is seen that after a first action, i.e., deployment of an implant, historical intervention data 902 records include procedural data related to procedural steps not yet taken, i.e., a next step.

Historical intervention data 902 may also include outcome data that is not part of current intervention data 904. Outcome data may include information about the post-procedure outcomes for the patient that underwent the past catheterization procedures. For example, intra-procedure result data or inter-procedure result data may include information describing the anatomical and/or physiological result of the past catheterization procedures, either during or after the past catheterization procedures. An example of intra-procedure result data includes information about angiographic results taken during the past catheterization procedures. For example, contrast medium may be delivered to the treated anatomical site and fluoroscopic images may be captured to assess whether the anatomical site is properly treated (good angiographic result). An example of inter-procedure result data includes information about a readmission rate for the patient following the past catheterization procedure. For example, the number of days between the past catheterization procedure and a subsequent hospitalization of the patient may be tracked. A readmission rate is a category of data used to determine quality of care, and thus may be used as an indicator for whether the procedural actions taken during the past catheterization procedures can be successfully leveraged to recommend next steps in the current catheterization procedure. Other outcome data may include anatomical measures, such as target vessel failure or target lesion failure, as well as measures of symptoms related to procedural success, such as the presence of angina.

In addition to the outcome data noted above, other procedural outcomes may be included in the historical intervention data. Among the relevant procedural outcome characteristics that may be included are by way of example, and not limitation: post-procedure minimal luminal diameter (MLD), post-procedure percent diameter stenosis, post-procedure TIMI flow, presence of an aneurysm, presence of a perforation, presence of a distal embolism, presence of a dissection (including dissection length or location), or presence overlap between implanted stents/scaffolds (including overlap length). These and other procedural outcome characteristics will be understood by one skilled in the art and may be captured for evaluation according to this description.

Referring again to FIG. 8, at operation 804, server 204 may receive current intervention data 904 from client 202 and store the received data in intervention case history database 208. A current intervention data 904 record in intervention case history database 208 may include current case data, current patient data, current anatomical data, or current device data, which may be manually input in catheterization lab 100 in any of the manners described above.

At operation 806, server 204 may receive image data corresponding to the images captured by imaging equipment during the current catheterization procedure. For example, the image data may correspond to deployment of medical device 602 during the catheterization procedure as described above. Image data may be a portion of current intervention data 904, and image data may include image files. The image data may be stored directly in intervention case history database 208 along with the other received current intervention data 904, or alternatively, the image data may be stored separately as image files apart from intervention case history database 208.

At operation 808, the image data is analyzed to determine additional intervention data representative of the current catheterization procedure. For example, the image files stored on server 204 may be analyzed using image analysis software 314 to determine additional intervention data representative of the current catheterization procedure. The additional intervention data may include additional anatomical data or additional deployment data representative of the current catheterization procedure. Derived additional deployment data may include a degree of malapposition of a medical device 602 deployed at a target anatomical site or a gap distance between the medical device 602 and the anatomical site. Derived additional anatomical data may include dimensions of the target anatomical site, the degree, eccentricity, and length of calcification at the anatomical site, or the presence of multi-vessel disease.

Figure 10:
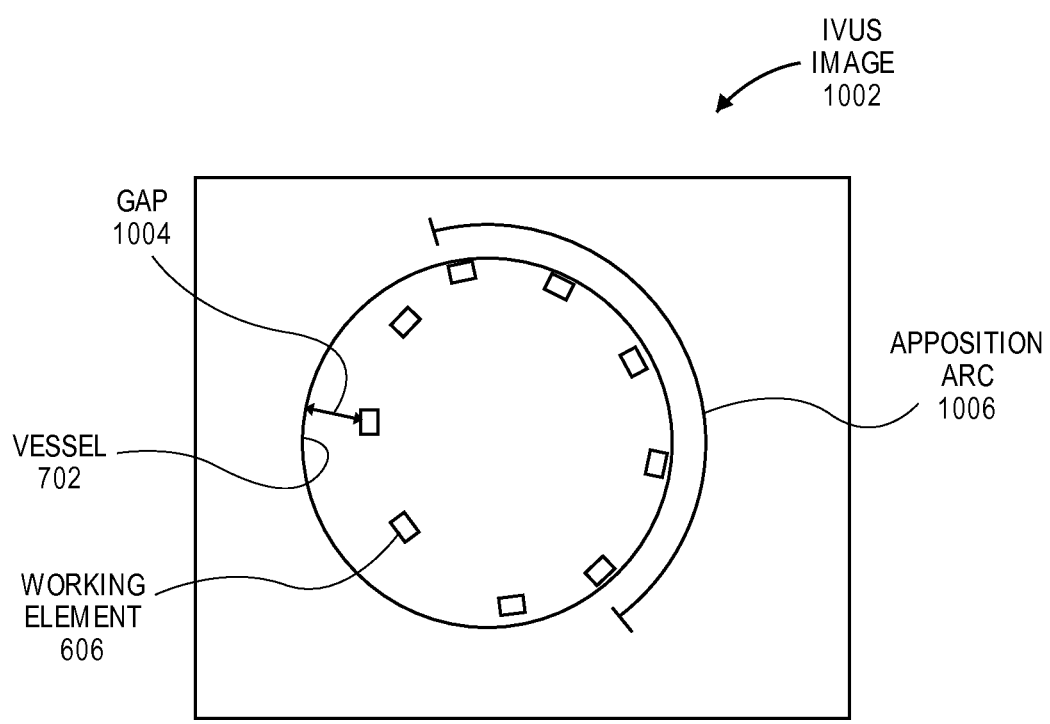
FIG. 10 shows image data stored at a server device in accordance with an embodiment.

Referring to FIG. 10, image data stored at a server device is shown in accordance with an embodiment. The captured image is an IVUS image 1002 captured by an IVUS system in catheterization lab 100. IVUS image 1002 provides an intravascular visualization of a target anatomical site, and as shown in this example, working element 606, which may be an implant, has been deployed at the anatomical site, which may be vessel 702, during the current catheterization procedure. It will be appreciated that IVUS image 1002 represents only one example of the types of images that may be captured and analyzed. For example, an OCT image may be captured and analyzed to assess a degree of calcification of a vessel prior to crossing the lesion with a guidewire. Thus, images may be captured before or after device deployment.

In general, the captured images may be analyzed using known image analysis techniques to identify additional intervention data such as physical structures that are represented in the images. For example, image analysis may be applied to IVUS image 1002 in FIG. 10 to determine the geometry of vessel 702 and working element 606. Based on these identified structures, various measurements may be performed to determine characteristics such as a gap 1004 between struts of the deployed implant and the inner wall of vessel 702. In addition, an apposition arc 1006 may be defined as an arc length along the inner wall at which the implant is in direct apposition (or within a predetermined distance of) the inner wall. Myriad other characteristics may be determined from the image data depending on the type of catheterization procedure and the critical information in assessing how to approach treatment and/or whether the procedure was successful, and those characteristics may be used as algorithm inputs to determine other useful data to be stored in intervention case history database 208. For example, gap 1004 and apposition arc 1006 data may be used to determine current deployment data such as a degree of malapposition of working element 606 of medical device 602 deployed at the anatomical site. Furthermore, as described above, morphological information, such as side branch involvement, may be automatically determined using image analysis.

Many techniques for image analysis are available, and so, an exhaustive description of such techniques shall not be provided. However, by way of example, image analysis techniques may include quantitative coronary angiography (QCA) techniques that permit quantification of vessel morphology. Such techniques may include some form of image processing that allows for computer-assisted definition and quantification of disease severity. Quantification may be performed digitally, using computer analysis of the images stored in an image processing system.

An image processing system may employ various methods of image processing. For example, thresholding may be used for image segmentation. That is, a grayscale image, such as a cineaniographic image, may be converted to a binary image to rapidly distinguish an inner lumen of a vessel from a vessel wall. The binary image may then be processed to determine a diameter of the lumen. Similarly, thresholding may be used to distinguish an implant, e.g., a stent, from the vessel wall and therefore to determine malapposition between the vessel wall and the stent, which will be identified as a gap between the two objects.

Additional techniques that may be relevant to image processing of captured images includes object recognition. That is, captured images may include captured video, i.e., a time series of individual images, and thus, video may be stored for processing. More particularly, object recognition techniques may be employed to identify a moving object, e.g., an implanted clip during a cardiac cycle will move, and to make measurements of the object.

Further still, image processing techniques may be used to make sense of multiple image data sets. For example, image registration may be used to convert different sets of image data into a single coordinate system. Such techniques may allow for images taken by different imaging modalities to be compiled into a single data set for comparison of different measurements, e.g., multiple lumen diameter measurements taken along the length may be compiled into a mean lumen diameter measurement. Any of the image processing techniques described above, and others known in the art, may be combined and employed to process the captured images and generate the additional data.

The current intervention data 904, including the transmitted data and the additional data derived from the transmitted data using analytic software at server 204, may be stored in intervention case history database 208. As with historical intervention data 902, the current intervention data 904 may be stored as a data record corresponding to a unique identifier, e.g., UCI, which uniquely identifies the data record. Thus, historical intervention data 902 records and current intervention data 904 record may be treated as data sets and analyzed using, e.g., predictive analysis and affinity analysis, to generate decision support data that may be useful to the operator for performing the current catheterization procedure successfully.

Referring again to FIG. 8, at operation 810, historical intervention data 902 and current intervention data 904 are analyzed to determine a similarity between the current catheterization procedure and one or more, i.e., a subset, of past catheterization procedures. Complex analytics may be employed to determine the similarity. The range of analytical models that may be used for this purpose will be understood by one skilled in the art, and a general example of one manner of determining the similarity is provided here, by way of example.

In an embodiment, determining the similarity between the current catheterization procedure and a subset of the past catheterization procedures includes identifying matching data values of historical intervention data 902 and current intervention data 904 in intervention case history database 208. For example, current intervention data 904 record, which includes data transmitted from catheterization lab 100, and additional current intervention data 904 generated by analysis of image data at server 204, may include values that are determined to match (or be within a predetermined range of) corresponding values in historical intervention data 902 records. By way of example, referring again to FIG. 9, it will be seen that the historical intervention data 902 record corresponding to UCI number "20140813B15" includes historical intervention data 902 with some values matching corresponding values of current intervention data 904 record (see matching values of patient data (age and sex), anatomical data (diameter and lesion type), and device data (device type and device size)). Furthermore, those records include additional intervention data generated by image analysis at server 204 with matching values (see apposition percentage considered to be a match when within a predetermined range—10% here—of each other).

In an embodiment, each set of matching corresponding data values may be assigned an individual similarity score. For example, different data types may be considered to have a larger impact on predicting successful procedural outcomes, and thus, matching values for those data types may be weighted more heavily in calculating the similarity between past and current procedures. As an example, each set of corresponding values may be assigned a matching score of either one (indicating a match or being within a predetermined range of each other) or a zero (indicating no match or not within the predetermined range of each other). The matching score may then be modified based on a weighting factor assigned to the data type. For example, a weighting factor for certain patient data, e.g., age and sex, may be 0.05 in a range of 0 to 1.0, indicating that the age of a patient is not the most important factor in predicting a clinical outcome of the current procedure if procedural steps are followed that were also applied during the matching past procedures. By contrast, a weighting factor for certain anatomical data, e.g., vessel diameter, may be 0.15, indicating that a size of the target anatomy is a relatively important factor in predicting an outcome of the current procedure when procedural steps are followed that were applied during the matching past procedure. The weighting factors may be any value, e.g., integer or decimal value, that can be multiplied against the matching score to generate an individual similarity score for each data type.

Weighting factors may represent a proportionate importance of each data type in intervention case history database 208. For example, the combination of all data types may be considered to have full importance (100% importance), and each data type may be determined to represent a percentage importance (i.e., as a percentage of one-hundred percent). As an example, in an embodiment in which intervention case history database 208 includes data values for the following data types, the data types may have the percentage importance indicated in respective parentheses: patient-specific history (5%), access site (5%), vessel location (10%), vessel diameter (15%), lesion length (5%), degree of tortuosity (10%), degree of calcification (10%), bifurcation/side-branch involvement (5%), degree of stenosis (5%), details of lesion preparation (15%), and degree of scaffold malapposition (15%). The percentage importance of the data types sum to full importance, i.e., 100%, and thus the weighting factors may be indicative of a proportionate importance of the data type as opposed to an absolute importance of the data type in predicting future outcomes.

Individual similarity scores may be processed further to arrive at a similarity score for a past catheterization procedure. For example, the individual similarity scores of all data types may be summed to generate a similarity score for a particular historical intervention data 902 record. Referring back to the example of comparing the historical intervention data 902 record corresponding to UCI number "20140813B15" with the current intervention data 904 record corresponding to UCI number "20150316B08," it will be appreciated that there are seven sets of matching data values (including the apposition percentage value being within 10% of each other) and thus, the similarity score between the procedures may be a score of 7 (assuming that no weighting factors are applied to the matching scores). By contrast, a comparison of the historical intervention data 902 record corresponding to UCI number "20140922P02" with the current intervention data 904 record corresponding to UCI number "20150316B08" determines that there are no matching data values, and thus, the similarity score between the procedures is 0. A threshold similarity score, e.g., a similarity score of 5, may be predetermined to indicate that past catheterization procedures have a similarity to the current catheterization procedure. Thus, the historical intervention data 902 record corresponding to UCI number "20140813B15" may be determined to have a similarity to the current intervention data 904 record, while the historical intervention data 902 record corresponding to UCI number "20140922P02" may be determined to not have the similarity to the current intervention data 904 record.

At operation 812, after determining a subset of the historical intervention data 902 records having the similarity to the current intervention data 904 record (which in the above example includes the historical intervention data 902 record corresponding to UCI number "20140813B15"), decision support data may be transmitted from server 204 to client 202. Decision support data may include a portion of historical intervention data 902 records corresponding to the subset of past catheterization procedures having the similarity to the current catheterization procedures. For example, the decision support data may include procedural data and/or outcome data that is present in the historical records and absent from the current record, which may help an operator select the most appropriate size and characteristics of a subsequent implant device or accessory device, as well as next procedural steps to achieve the same historical outcomes.

The receipt of current intervention data 904 and historical intervention data 902 may occur continuously such that server 204 continuously updates the intervention case history database 208 with new data being generated by catheterization labs across different geographies. This constant updating may occur as respective catheterization lab personnel input data, e.g., patient data, procedural data, and scan barcodes encoding data, e.g., UDI of devices used in the ongoing procedures. Furthermore, automated analysis of the database information using concept exploration, natural language processing and identification, quantitative image analysis, content-based image retrieval, visual content recognition, and machine learning methods embodied in software applications 210 may occur in real-time to allow for the identification of similar procedures and the provision of corresponding data while the current catheterization procedure is being performed. For example, transmission of the decision support data from server 204 to client 202 may occur within an interval from the transmission of current intervention data 904 from client 202 to server 204 such that the catheterization procedure is not disrupted. In an embodiment, the provision of decision support data by server 204 occurs within 5 minutes of server 204 receiving the current intervention data 904, which is a short enough window to not disrupt the flow of interventional cases in catheterization lab 100. For example, the exchange of intervention data and decision support data between client 202 and server 204 may occur in less than 5 seconds.

Figure 11:
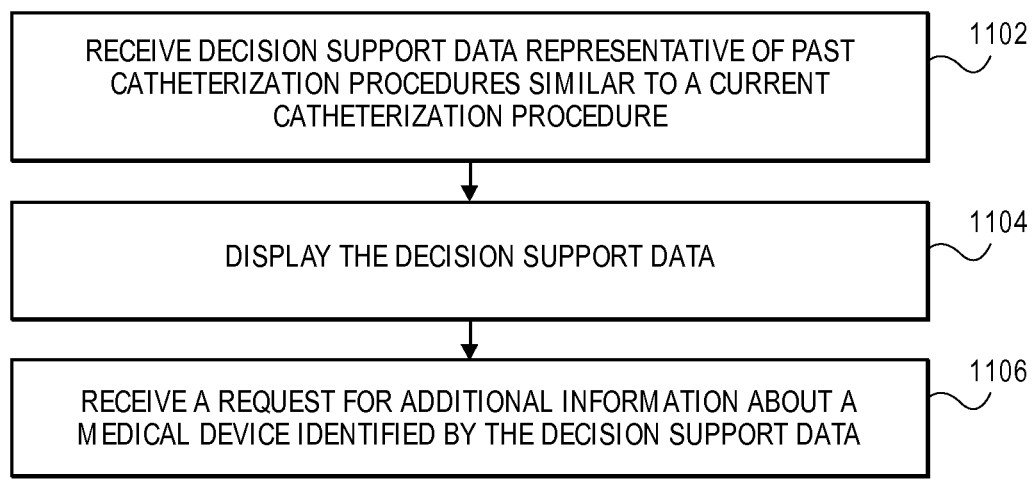
FIG. 11 is a flowchart of a method to receive and display decision support data to facilitate clinical decisions during a catheterization procedure in accordance with an embodiment.

Referring to FIG. 11, a flowchart of a method to receive and display decision support data to facilitate clinical decisions during a catheterization procedure is shown in accordance with an embodiment. At operation 1102, client 202 in catheterization lab 100 receives the decision support data associated with historical intervention data 902 that was determined to be similar to current intervention data 904. In an embodiment, the decision support data is aggregated by server 204 prior to transmission, such that client 202 receives a simple set of procedural options and associated outcomes instead of an entire data set to be processed further at client 202. For example, aggregation by server 204 may involve recommending the next procedural step, e.g. post-dilatation, and the associated percutaneous transluminal angioplasty (PTA) catheter, and calculating a recommended inflation pressure, where the recommended inflation pressure is the average inflation pressure used in past catheterization procedures having similarity to the current catheterization procedure and also having favorable clinical outcomes. Aggregation by server 204 may also involve calculating an average or median intra-procedure or inter-procedure result, e.g., a median intra-procedure angiographic result or an average inter-procedure 30-day readmission rate, for the entire subset of historical intervention data 902 found to be similar to current intervention data 904, and provide the average or median value as a single data value for display in catheterization lab 100.

In an embodiment, predictive analytics may be employed by predictive analysis software application 214 to generate predictive models that analyze the available historical intervention data 902 and current intervention data 904, e.g., procedural data available for both, in order to make predictions about future outcomes if a similar procedure is followed in the current catheterization procedure as was followed in similar past catheterization procedures. Thus, aggregation may utilize any algorithm that takes the subset of historical intervention data 902 as an input to generate an output about what a next step in the current catheterization procedure could be, what the likely acute procedural outcome will be if the next step is taken, and risks for longer-term outcomes.

At operation 1104, the decision support data may be displayed to the operator in catheterization lab 100 to support decisions about how to proceed with treatment of the patient. The aggregated dataset transmitted from server 204 to client 202 can be presented to the operator as a simple set of procedural options and associated acute procedural outcomes and risks of longer-term outcomes.

Figure 12A:
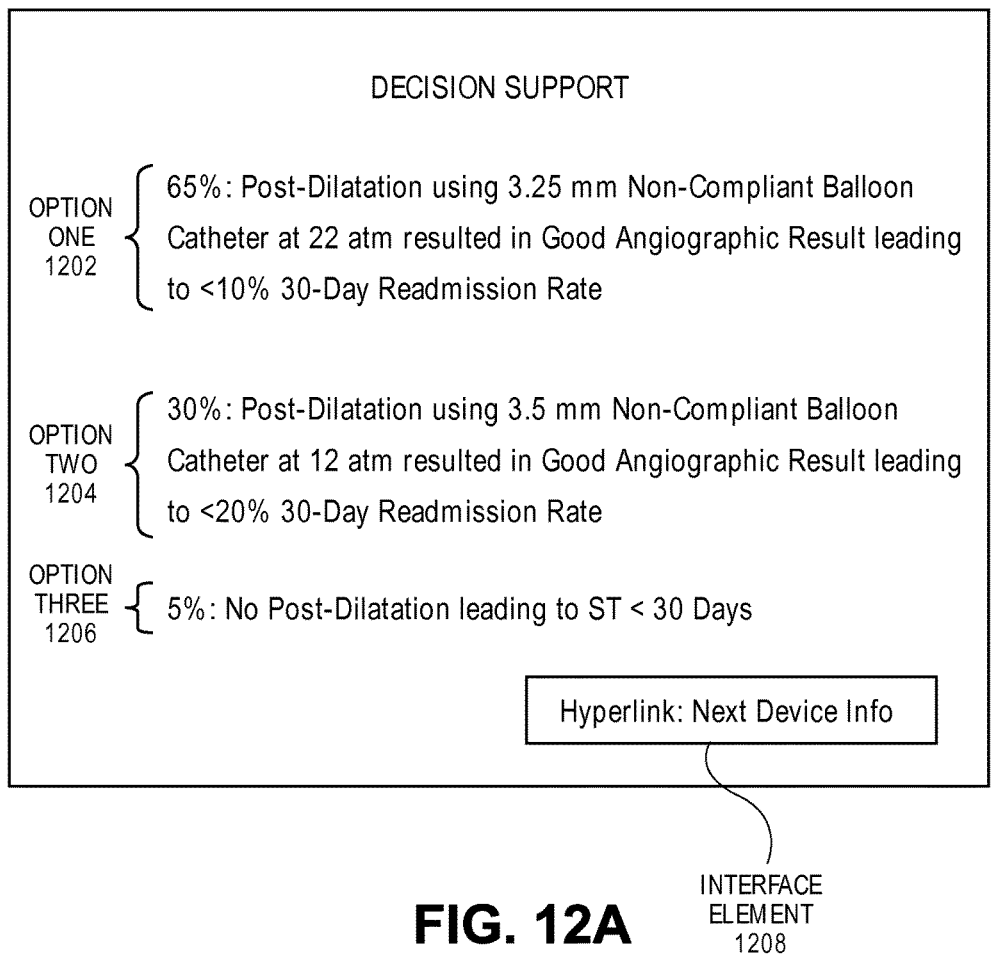
FIGS. 12A-12C show various graphical user interfaces to display decision support data in accordance with an embodiment.

Referring to FIG. 12A, a graphical user interface to display decision support data is shown in accordance with an embodiment. As described above, decision support data may be displayed on display device 106 in catheterization lab 100. Decision support data may be displayed on multiple displays, e.g., on one of four video displays 106 in catheterization lab 100, on a tablet device in the catheterization lab 100, on an optical head mounted display worn by the operator, etc. In an embodiment, a decision support display provides information to the operator that includes procedural steps used in similar historical procedures and a predicted acute procedural outcome as well as longer-term outcomes if the procedural steps are followed. For example, after deploying a stent implant in vessel 702 and capturing images of the deployed implant, as the operator is retrieving the stent delivery catheter from the anatomy, the image data and current intervention data 904 are sent to server 204. Then, as the operator is viewing the image data and considering the next procedural step to take based on his own set of experience and knowledge, the decision support display may provide one or more procedural actions that have been taken in other similar cases and their likely outcomes. For example, a first option 1202 may be to perform post-dilatation using a 3.25 mm non-compliant balloon catheter at 22 atm. This option may have been performed by a certain percentage of a subset of historical intervention data 902 that was found to be similar to the current intervention data 904 (65% of the subset may have taken this next step as indicated in FIG. 12A). Of that percentage, the intra-procedure angiographic result may have been all or mostly good, and less than 10% may have had a poor intra-procedure results, e.g. additional procedural steps necessary to get a good acute result or poor post-procedure result, e.g., a 30-day readmission.

One or more other options may be presented also. For example, a second option 1204 may be to perform post-dilatation using a 3.5 mm non-compliant balloon catheter at 12 atm. This option may have been performed by 30% of the subset of historical intervention data 902 that was found to be similar to the current intervention data 904. Of that percentage, the intra-procedure angiographic result may have been all or mostly good, and less than 20% may have had a poor intra-procedure results, e.g. additional procedural steps necessary to get a good acute result or poor post-procedure result. In viewing option one 1202 and option two 1204, the operator may choose to follow the procedural steps presented in option one 1202 based on the statistically better outcome that it predicts. However, the operator may also choose to follow option two 1204, for example, because it aligns better with his experience and still predicts an intra-procedure and/or post-procedure outcome that he believes is favorable.

The presented options may also include options that predict unfavorable outcomes, but which are nonetheless presented to help guide the operator away from choosing such a course of action if his experience and knowledge would lead him that way in spite of the substantially better options presented. For example, a third option 1206 may be to not perform post-dilatation. This option may have been performed by 5% of the subset of historical intervention data 902 that was found to be similar to the current intervention data 904. Of that percentage, the post-procedure result may have been predominantly poor, e.g. intra-procedure results, e.g. additional procedural steps necessary to get a good acute result or poor post-procedure result i.e., stent thrombosis and/or readmission in less than 30 days for all or most of the cases. Thus, an operator is likely to be dissuaded from pursuing a similar treatment path, and instead may favor one of the other options that predict better outcomes and are more consistent with the standard of care, even if the third option is his usual manner of treatment.

In an embodiment, therefore, at the end of the evaluation process a physician operator may be presented with several treatment options, their expected outcomes, and how strongly each option is supported by the current SCAI/AHA/ACC guidelines. That is, the level of support (or the level of evidence) for pursuing a possible treatment route may be given to the operator to allow the operator to make an informed decision about how best to treat the patient.

Outcome data, e.g., intra-procedure result data or post-procedure result data, may be presented according to a preference of an operator. For example, the operator may be interested in viewing shorter term outcomes and longer term outcomes, and furthermore, may desire to view shorter term outcomes before longer term outcomes. Thus, outcome data may present decision support data such that the shortest term data, e.g., acute procedural success, would precede the longer term data, e.g., 30-day readmissions. It will also be appreciated that result data may be filtered to include different outcome term ranges. For example, in addition or in the alternative to providing 30-day readmission data, the decision support tool may provide 1-year, 3-year, and 5-year major adverse cardiac events (MACE) data. Accordingly, the above examples of relevant outcome data is not to be viewed as restrictive.

Decision support data may be filtered and/or focused by stratifying the historical database records that are used in the determination of decision support data. More particularly, the portion of the historical database being used to drive the comparison of past and present data to produce decision support data may be a subset of the overall historical data set. For example, only data for a particular site, e.g., a particular hospital, or a particular subset of operators, e.g., high-volume operators who provide more than 300 PCI procedures per year or more than 50 heart valve clip implantation procedures per year, may be used in the data analysis. Such stratification of the historical data may be used to improve the relevancy of the decision support data that is generated by the decision support tool, and may be refined through an iterative approach.

Device data displayed to the operator may be generic. That is, although manufacturer information may be tracked in the intervention case history database 208, the information about treatment options and devices used in the decision support data may not identify the specific medical device manufacturer. The decision support tool may, however, provide the operator with the option to learn more about suitable devices from a specific manufacturer.

Referring again to FIG. 11, at operation 1106, the operator may request additional information for an interventional device identified in the decision support data shown in FIG. 12A. The decision support display may allow the operator to navigate to additional information that can assist in making procedural decisions. For example, user interface elements 1208 (e.g., hyperlinks) on the decision support display may be selectable to result in the display of more decision support data. In an embodiment, selection of a hyperlink on the decision support display causes the display of information about the next device recommended in one or more of the options. The additional decision support data may include manufacturer-specific devices that meet the device criteria, e.g., size, identified in the decision support options.

Figure 12B:
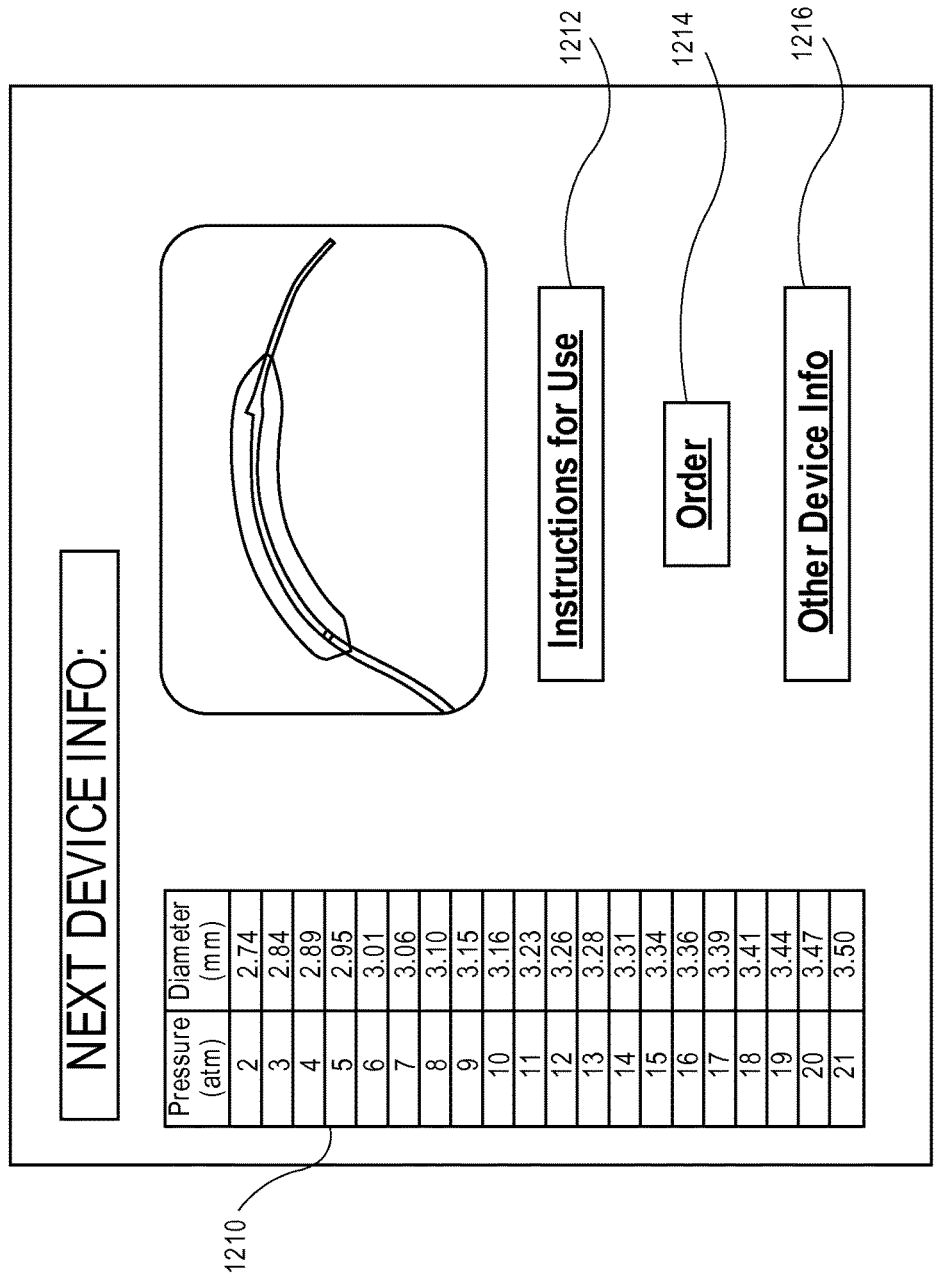

Referring to FIG. 12B, a graphical user interface to display decision support data is shown in accordance with an embodiment. With respect to option one 1202 discussed above, the 3.25 mm non-compliant balloon may be associated with manufacturer-specified device characteristics, including a compliance chart 1210 or an instruction for use 1212. These device characteristics may be displayed to the operator. Other device characteristics may be displayed specific to the device that is being considered for use. For example, the operator may be considering a guidewire for use in crossing a lesion, and thus, device characteristics displayed for the guidewire may include guidewire tip loads, guidewire support level, etc.

In an embodiment, an ordering element 1214 may be provided by the user interface to allow the operator to select the device for use, e.g., to "order" the device. The display may identify information about the manufacturing of the product, e.g., manufacturer name, product brand, trademark information, etc., to assist the operator in making decisions about the quality of the product and whether to order more units. Selecting "order" may trigger a notification to be sent to the catheterization lab 100 administrator or inventory database to adjust the inventory list of the catheterization lab 100 and/or to trigger an order of devices of the selected types from the indicated manufacturer to stock or restock the device.

Based on the device data identified from the subset of similar historical procedures, or based on the selection of a particular device for the next procedural step by the operator, an accessory device may be identified. As an example, server 204 may use affinity analysis software application 216 to determine accessory devices that the operator may find useful in the current catheterization procedure. After selecting a device information element 1216 provided by the user interface, information about the identified accessory devices may be displayed.

Figure 12C:
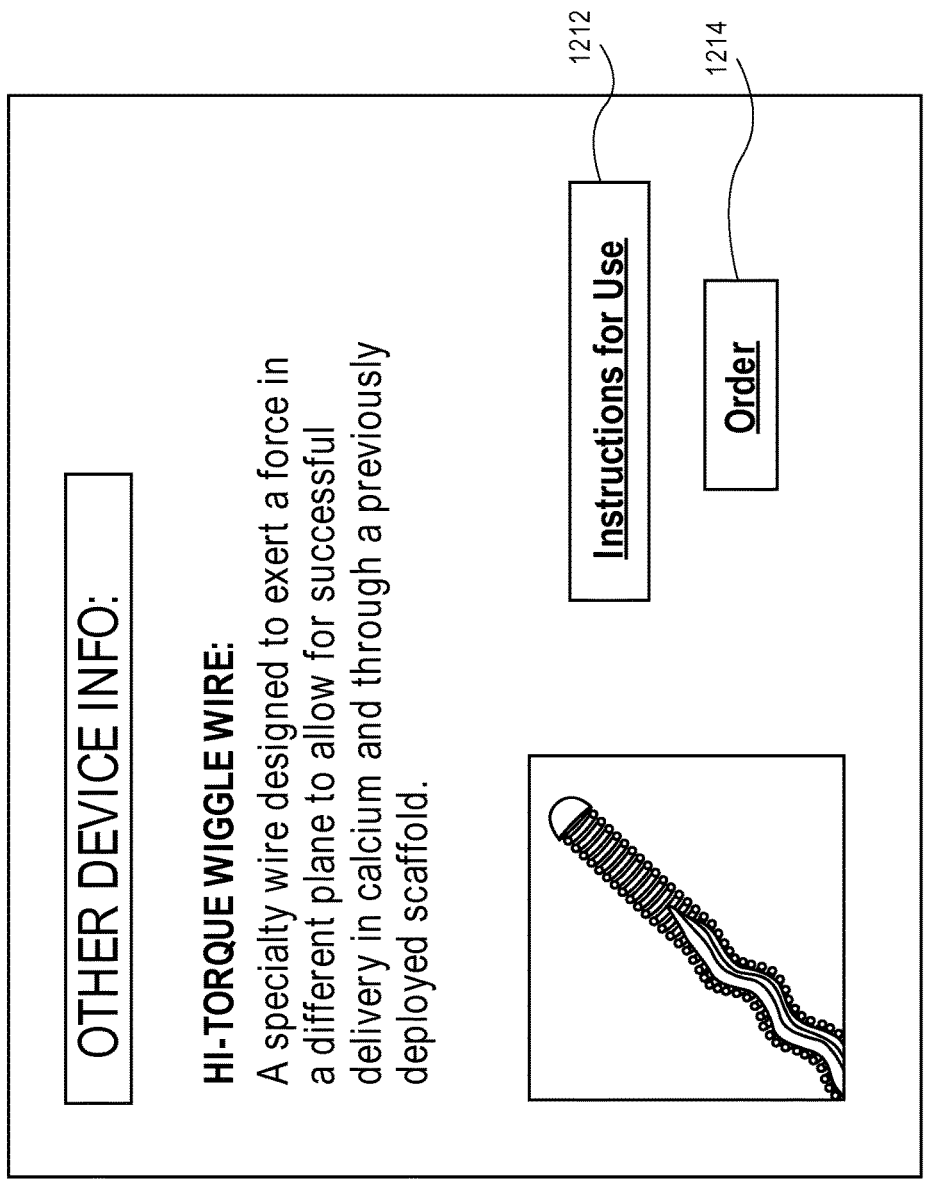

Referring to FIG. 12C, a graphical user interface to display decision support data is shown in accordance with an embodiment. For example, the decision support data may include information about the design and intended use for an accessory device, such as a guidewire, PTA catheter or microcatheter. The display screen may also provide respective interface elements 1212, 1214 to allow the operator to "order" the accessory device or to view the associated instructions for use of the accessory device, similar to the functionality described above with respect to FIG. 12B.

The decision support tool described above may allow for additional data and information to be displayed to the operator on demand. For example, the operator may be allowed to select one or more user elements of the graphical user interface to cause client 202 to retrieve and display current guidelines in real-time. More particularly, the operator may be able to search for current guideline information through the decision support tool and to access the guidelines for display during the current catheterization procedure. Such guidelines may complementary to the information described above. For example, referring again to FIG. 11, an additional operation may allow the operator to request additional information for guidelines relevant to the current catheterization procedure. The guidelines may, for example, be returned in response to a search query directed to a database having guideline information stored locally or at a remote server. Alternatively, the guidelines may be returned with decision support data, for example, where the historical data includes guidelines relevant to the past catheterization procedures stored as records corresponding to the historical data. In either case, the guidelines that are returned to the operator may provide suggestions for interventional steps. The guideline suggestions may be presented alongside the other decision support data to allow the interventionist to quickly review the suggestions while standing at the patient platform 102.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method to facilitate clinical decisions during a catheterization procedure, the method comprising:
    storing, in an interventional case history database, historical intervention data representative of past catheterization procedures and based on images taken during the past catheterization procedures;
    receiving, concurrently with a current catheterization procedure being performed in a catheterization lab, an image taken by an intravascular imaging system during the current catheterization procedures;
    comparing, by a data processing system, the historical intervention data based on images taken during the past catheterization procedures to current intervention data based on the image taken during the current catheterization procedure to determine a subset of past catheterization procedures having images similar to the image;
    determining decision support data including a plurality of procedural options for the current catheterization procedure, wherein the plurality of procedural options include respective procedural actions and associated likely clinical outcomes, and wherein the likely clinical outcomes are based on clinical outcomes of respective percentages of the subset of past catheterization procedures when the associated procedural actions were performed; and
    transmitting the decision support data for display of the plurality of procedural options including the respective procedural actions and associated likely clinical outcomes by a monitor in the catheterization lab during the current catheterization procedure.

2. The method of claim 1, wherein the historical intervention data includes one or more of historical patient data, historical anatomical data, historical device data, historical deployment data, historical procedural data, or historical outcome data representative of the past catheterization procedures, and wherein the current intervention data includes one or more of current patient data, current anatomical data, current device data, or current deployment data representative of the current catheterization procedure.

3. The method of claim 2, wherein the current intervention data includes image data representing an anatomical site being accessed during the current catheterization procedure; and further comprising:
    analyzing the image data to determine the current anatomical data or the current deployment data.

4. The method of claim 3, wherein the current anatomical data includes one or more of a dimension of the anatomical site, a degree of calcification of the anatomical site, or a degree of eccentricity of the anatomical site, and wherein the current deployment data includes one or more of a degree of malapposition of a stent implant deployed at the anatomical site or a gap distance between the stent implant and the anatomical site.

5. The method of claim 2, wherein the respective procedural actions are to be performed during the current catheterization procedure.

6. The method of claim 5, wherein the likely clinical outcomes include one or more of a median intra-procedure result or an average inter-procedure result when the associated procedural actions were performed during the subset of past catheterization procedures.

7. The method of claim 1 further comprising:
    determining similarity between the current catheterization procedure and the subset of past catheterization procedures based on one or more matching data values of the historical intervention data and the current intervention data.

8. The method of claim 7, wherein determining the similarity includes:

identifying one or more sets of historical data values of the historical intervention data matching corresponding current data values of the current intervention data;

assigning a similarity score to each set of matching data values; and determining the similarity between the current catheterization procedure and the subset of past catheterization procedures based on the similarity scores.

9. The method of claim 1, wherein the historical intervention data is stored at a location remote from the current catheterization procedure.

10. The method of claim 9, wherein transmitting the decision support data occurs within 5 minutes of receiving the image at the location.

11. A non-transitory machine-readable storage medium storing instructions, which when executed by one or more processors of a decision support computer, causes the decision support computer to perform a method comprising:

storing, in an interventional case history database, historical intervention data representative of past catheterization procedures and based on images taken during the past catheterization procedures;

receiving, concurrently with a current catheterization procedure being performed in a catheterization lab, an image taken by an intravascular imaging system during the current catheterization procedure;

comparing, by one or more processors of the decision support computer, the historical intervention data based on images taken during the past catheterization procedure to current intervention data based on the image taken during the current catheterization procedure to determine a subset of past catheterization procedures having images similar to the image;

determining decision support data including a plurality of procedural options for the current catheterization procedure, wherein the plurality of procedural options include respective procedural actions and associated likely clinical outcomes, and wherein the likely clinical outcomes are based on clinical outcomes of respective percentages of the subset of past catheterization procedures when the associated procedural actions were performed; and transmitting the decision support data for display of the plurality of procedural options including the respective procedural actions and associated likely clinical outcomes by a monitor in the catheterization lab during the current catheterization procedure.

12. The medium of claim 11, wherein the historical intervention data includes one or more of historical patient data, historical anatomical data, historical device data, historical deployment data, historical procedural data, or historical outcome data representative of the past catheterization procedures, and wherein the current intervention data includes one or more of current patient data, current anatomical data, current device data, or current deployment data representative of the current catheterization procedure.

13. The medium of claim 12, wherein the current intervention data includes image data representing an anatomical site being accessed during the current catheterization procedure, and further comprising:

analyzing the image data to determine the current anatomical data or the current deployment data.

14. The medium of claim 13, wherein the current anatomical data includes one or more of a dimension of the anatomical site, a degree of calcification of the anatomical site, or a degree of eccentricity of the anatomical site, and wherein the current deployment data includes one or more of a degree of malapposition of a stent implant deployed at the anatomical site or a gap distance between the stent implant and the anatomical site.

15. The medium of claim 12, wherein the respective procedural actions are to be performed during the current catheterization procedure.

16. The medium of claim 15, wherein the likely clinical outcomes include one or more of a median intra-procedure result or an average inter-procedure result when the associated procedural actions were performed during the subset of past catheterization procedures.

17. The medium of claim 11 further comprising:

determining similarity between the current catheterization procedure and the subset of past catheterization procedures based on one or more matching data values of the historical intervention data and the current intervention data.

18. The medium of claim 17, wherein determining the similarity includes:

identifying one or more sets of historical data values of the historical intervention data matching corresponding current data values of the current intervention data;

assigning a similarity score to each set of matching data values; and determining the similarity between the current catheterization procedure and the subset of past catheterization procedures based on the similarity scores.

19. The medium of claim 11, wherein the historical intervention data is stored at a location remote from the current catheterization procedure.

20. The medium of claim 19, wherein transmitting the decision support data occurs within 5 minutes of receiving the image at the location.

21. A non-transitory machine-readable storage medium storing instructions, which when executed by one or more processors of a decision support computer, causes the decision support computer to perform a method comprising:

sending, during a current catheterization procedure being performed in a catheterization lab, an image taken by an intravascular imaging system during the current catheterization procedure; and receiving decision support data for display by a monitor in the catheterization lab during the current catheterization procedure, wherein the decision support includes a plurality of procedural options for the current catheterization procedure, wherein the procedural options include respective procedural actions and associated likely clinical outcomes, wherein the likely clinical outcomes are based on clinical outcomes or respective percentages of a subset of past catheterization procedures when the associated procedural actions were performed, wherein the subset of past catheterization procedures are based on a comparison of historical intervention data based on imaged taken during the subset of past catheterization procedures to current intervention data based on the image taken during the current catheterization procedure.

22. The medium of claim 21, wherein the historical intervention data includes one or more of historical patient data, historical anatomical data, historical device data, historical deployment data, historical procedural data, or historical outcome data representative of the past catheterization procedures, and wherein the current intervention data includes one or more of current patient data, current anatomical data, current device data, or current deployment data representative of the current catheterization procedure.

23. The method of claim 22, wherein the current intervention data includes image data representing the anatomical site being accessed during the current catheterization procedure; and further comprising:
 analyzing the image data to determine the current anatomical data or the current deployment data.

24. The medium of claim 23, wherein the current anatomical data includes one or more of a dimension of the anatomical site, a degree of calcification of the anatomical site, or a degree of eccentricity of the anatomical site, and wherein the current deployment data includes one or more of a degree of malapposition of the stent implant deployed at the anatomical site or a gap distance between the stent implant and the anatomical site.

25. The medium of claim 22 further comprising:
 displaying, by the monitor in the catheterization lab during the current catheterization procedure, the plurality of procedural options for the current catheterization procedure.

26. The medium of claim 25, wherein the received decision support data includes the likely clinical outcomes having one or more of a median intra-procedure result or an average inter-procedure result when the respective procedural action was performed during the subset of past catheterization procedures, and further comprising:
 displaying one or more of the median intra-procedure result or the average inter-procedure result.

\* \* \* \* \*